United States Patent [19]
Hofheinz et al.

[11] Patent Number: 5,948,791
[45] Date of Patent: Sep. 7, 1999

[54] QUINOLINE DERIVATIVES FOR TREATING MALARIA

[75] Inventors: Werner Hofheinz, Bottmingen; Raffaello Masciadri, Basel, both of Switzerland

[73] Assignee: Hoffmann-La Roche Inc., Nutley, N.J.

[21] Appl. No.: 08/747,173

[22] Filed: Nov. 12, 1996

[30] Foreign Application Priority Data

Nov. 16, 1995 [CH] Switzerland ............................. 3250/95

[51] Int. Cl.⁶ ....................... A61K 31/47; C07D 215/44
[52] U.S. Cl. ................ 514/313; 514/235.2; 514/253; 514/256; 514/314; 544/128; 544/238; 544/333; 544/405; 546/163
[58] Field of Search ............................. 546/163; 514/313, 514/314, 235.2, 228.8, 253; 544/63, 96, 238, 333, 405, 128

[56] References Cited

U.S. PATENT DOCUMENTS

| | | | |
|---|---|---|---|
| 2,816,893 | 12/1957 | Jacob | 260/286 |
| 2,901,484 | 8/1959 | Schock | 260/286 |
| 5,510,356 | 4/1996 | Vennerstrom | 514/313 |

FOREIGN PATENT DOCUMENTS

| | | |
|---|---|---|
| WO 93 07126 | 4/1993 | WIPO . |
| WO 95 35287 | 12/1995 | WIPO . |
| WO 95 35288 | 12/1995 | WIPO . |

OTHER PUBLICATIONS

Singh T et al. J. Med. Chem. 14 (4), 283–286, 1971.

Vennerstrom Jl et al. J. Med. Chem. 35 (11), 2129–2134, 1992.

Goulding RW et al. J. Labelled compd. Radiopharm. 16 (1, secon Int. Symp. Radiopharm. Chem.), 46–48, 1979.

Jonathan L. Vennerstrom, et al., Journal of Medicinal Chemistry, vol. 35, No. 11, "Bisquinolines. 1. N,N–Bis(7–chloroquinolin–4–yl) alkanediamines with Potential against Chloroquine–Resistant Malaria" (1992), pp. 2129–2134.

Tara Singh, et al., Journal of Medicinal Chemistry, vol. 14, No. 4, "Antimalarials. 7–Chloro–4–(substituted amino) quinolines" (1971), pp. 283–286.

R.W. Goulding, et al., Chemical Abstract, vol. 92, No. 18031 "Radio–iodine labeled 4–amino–7–iodoquinolines for melanoma detection" (1980).

*Primary Examiner*—Evelyn Huang
*Attorney, Agent, or Firm*—George W. Johnston; Dennis P. Tramaloni; Alan P. Kass

[57] ABSTRACT

The invention relates to novel quinoline derivatives and their therapeutic use against malaria.

15 Claims, No Drawings

QUINOLINE DERIVATIVES FOR TREATING MALARIA

SUMMARY OF THE INVENTION

The present invention relates to quinoline derivatives of the formula

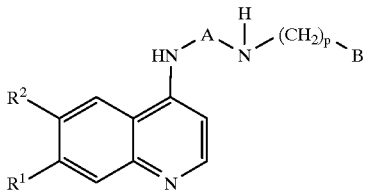
I wherein $R^1$ is halogen or trifluoromethyl;

$R^2$ is selected from the group consisting of hydrogen, halogen and trifluoromethyl;

A is

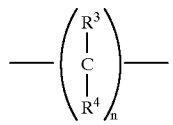

or $(C_5-C_6)$-cycloalkylene;

n is 1–4;

$R^3$ and $R^4$ are each independently hydrogen or methyl;

p is 0–3 and

B is aryl, as well as pharmaceutically acceptable salts of basic compounds of general formula I.

These quinoline derivatives are useful for the prophylaxis and treatment of malaria.

DESCRIPTION OF THE INVENTION

The invention is concerned with quinoline derivatives, especially $N_1$-aralkyl-$N_2$-quinolin-4-yl-diamine derivatives of the general formula

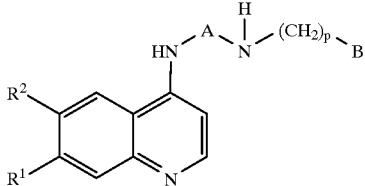
I wherein $R^1$ is halogen or trifluoromethyl;

$R^2$ is selected from the group consisting of hydrogen, halogen and trifluoromethyl;

A is

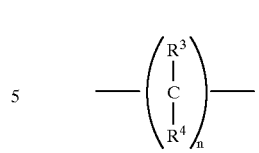

or $(C_5-C_6)$-cycloalkylene;

n is 1–4;

$R^3$ and $R^4$ are each independently hydrogen or methyl;

p is 0–3 and

B is aryl, as well as pharmaceutically acceptable salts of basic compounds of general formula I. All possible stereoisomers as well as their racemates are included in formula I.

A sub-group of compounds of formula I comprises those in which p is 1–3 and the other substituents have the significances given above.

These novel compounds have the property that they are active not only against chloroquine-sensitive, but also against chloroquine-resistant malaria pathogens. For this reason they are very well suited for the prophylaxis and treatment of malaria, especially in cases where the malaria pathogens are resistant to chloroquine.

Objects of the present invention are the mentioned compounds of formula I as well as their pharmaceutically usable salts thereof per se and as therapeutically active substances, the manufacture of these compounds and salts and their use for therapeutic purposes, especially for the prevention or treatment of malaria, as well as medicaments containing a compound of formula I or a salt thereof and the production of such medicaments.

The term "lower-alkyl" used in the present description denotes straight-chain or branched saturated hydrocarbon residues such as methyl, ethyl, n-propyl, isopropyl, n-butyl, isobutyl, s-butyl, t-butyl and the like. "Halogen" is chorine, bromine, fluorine or iodine.

When A in formula I is an aliphatic hydrocarbon chain, branched chains, for example —CH(CH$_3$)—CH$_2$—, —CH$_2$CH(CH$_3$)— or —CH$_2$C(CH$_3$)$_2$—, are especially preferred.

The term "cycloalkylene" embraces preferably cyclopentyl or cyclohexyl.

The term "aryl" embraces conveniently phenyl or substituted phenyl, with the number of substituents preferably being 1–3 and the substituents being selected from a group consisting of halogen, hydroxy, lower-alkyl, lower-alkoxy, CF$_3$, cyano, di-lower-alkylamino or their N-oxides, phenyloxy, phenyl or methylsulphanyl.

Furthermore, the term "aryl" conveniently embraces naphthyl, benzo[1,3]dioxol or mono- or bicyclic aromatic heterocycles with 1 or 2 hetero atoms, especially N and/or O, for example pyridyl, quinolyl or furyl. Rings such as phenyl, pyridin-2-yl, pyridin-3-yl, pyridin-4-yl, naphthalen-1-yl, naphthalen-2-yl, furan-2-yl, furan-3-yl or quinolin-4-yl are preferred.

Preferred compounds of general formula I are especially those in which $R^1$ is chlorine, $R^2$ is hydrogen, p is 1, A is —CH$_2$—C(CH$_3$)$_2$— and B is a benzene ring which is unsubstituted, mono-substituted or di-substituted.

Examples of such compounds are:

$N_1$-(7-Chloro-quinolin-4-yl)-$N_2$-(3-chloro-benzyl)-2-methyl-propane-1,2-diamine, $N_1$-(7-chloro-quinolin-4-yl)-$N_2$-(benzyl)-2-methyl-propane-1,2-diamine, $N_1$-(7-chloro-quinolin-4-yl)-$N_2$-(2-hydroxy-3-methoxy-benzyl)-2-methyl-propane-1,2-diamine, $N_1$-(7-chloro-quinolin-4-yl)-$N_2$-(2-hydroxy-5-methoxy-benzyl)-2-methyl-propane-1,2-diamine and $N_1$-(7-chloro-quinolin-4-yl)-$N_2$-(4-hydroxy-3-methoxy-benzyl)-2-methyl-propane-1,2-diamine.

Compounds of general formula I in which $R^1$ is chlorine, $R^2$ is hydrogen, p is 1 or 2, A is cyclohexane-1,2-diyl or cyclohexane-1,4-diyl and B is a benzene ring which is unsubstituted, mono-substituted, di-substituted or tri-substituted are also preferred.

Examples of such compounds are especially (1S,2S)-$N_1$-(7-chloro-quinolin-4-yl)-$N_2$-(benzyl)-cyclohexane-1,2-diamine, (1S,2S)-$N_1$-(7-chloro-quinolin-4-yl)-$N_2$-(4-chlorobenzyl)-cyclohexane-1,2-diamine, (1S,2S)-$N_1$-(7-chloro-quinolin-4-yl)-$N_2$-(4-dimethylamino-benzyl)-cyclohexane-1,2-diamine, cis-$N_1$-(7-chloro-quinolin-4-yl)-$N_4$-(4-dimethylamino-benzyl)-cyclohexane-1,4-diamine, cis-$N_1$-(7-chloro-quinolin-4-yl)-$N_4$-(benzyl)-cyclohexane-1,4-diamine, cis-$N_1$-(7-chloro-quinolin-4-yl)-$N_4$-(3-chloro-benzyl)-cyclohexane-1,4-diamine, cis-$N_1$-(7-chloro-quinolin-4-yl)-$N_4$-(2-hydroxy-4-methoxy-benzyl)-cyclohexane-1,4-diamine, cis-$N_1$-(7-chloro-quinolin-4-yl)-$N_4$-(3,5-dimethoxy-benzyl)-cyclohexane-1,4-diamine, cis-$N_1$-(7-chloro-quinolin-4-yl)-$N_4$-(4-methylsulphanyl-benzyl)-cyclohexane-1,4-diamine, cis-$N_1$-(7-chloro-quinolin-4-yl)-$N_4$-(4-diethylamino-benzyl)-cyclohexane-1,4-diamine, cis-$N_1$-(7-chloro-quinolin-4-yl)-$N_4$-(biphenyl-4-yl)methyl-cyclohexane-1,4-diamine, trans-$N_1$-(7-chloro-quinolin-4-yl)-$N_4$-[2-(3,5-dimethoxy-phenyl)-ethyl]-cyclohexane-1,4-diamine, cis-$N_1$-(7-chloro-quinolin-4-yl)-$N_4$-(4-methoxy-benzyl)-cyclohexane-1,4-diamine, trans-$N_1$-(7-chloro-quinolin-4-yl)-$N_4$-(4-dimethylamino-benzyl)-cyclohexane-1,4-diamine and trans-$N_1$-(7-chloro-quinolin-4-yl)-$N_4$-(2,6-difluoro-benzyl)-cyclohexane-1,4-diamine.

The novel compounds of formula I can be manufactured in accordance with the invention by a) reducing a Schiff's base of the general formula

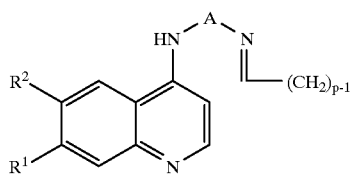

II wherein the substituents have the significance described above, or b) reacting an amine of the formula

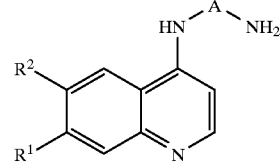

III with a compound of the formula

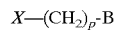   IV wherein X is a leaving group and the other substituents have the significance described above, or c) reacting a compound of the formula

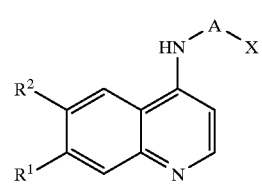

V with an amine of the formula

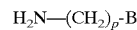   VI wherein all substituents have the significance described above, or d) reacting a ketone or an aldehyde of the formula

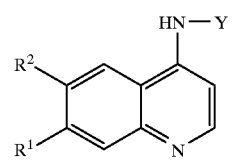

VII wherein Y is

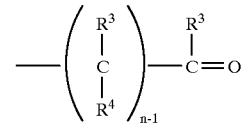

or oxo-($C_5$–$C_6$)-cycloalkyl
and $R^1$ and $R^2$ have the significance set forth above, with an amine of formula VI and a reducing agent, and e) if desired, converting the compound obtained into a pharmaceutically acceptable acid addition salt.

In accordance with process variant a) of the process in accordance with the invention a Schiff's base of formula II is reduced. Suitable reducing agents are complex hydrides, diborane, reactive metals or formic acid. The use of complex hydrides such as sodium borohydride is especially preferred. The reduction is carried out in a temperature range of 0 to 30° C., preferably at room temperature. Suitable solvents are alcohols or mixtures of alcohols with chlorinated hydrocarbons. Ethanol or an ethanol-dichloromethane mixture is preferred for the reduction with sodium borohydride. When formic acid is used as the reducing agent, formic acid or another dilute acid can also be used as the solvent.

Compounds of formula I are obtained according to process variant b) by reacting amines of formula III with compounds of formula IV. Halogen or aliphatic or aromatic sulphonyloxy groups are suitable as the leaving group X in formula IV. Conveniently, the reaction is carried out in a solvent, for example in an alcohol such as methanol or ethanol or in an aprotic solvent such as acetonitrile, N,N-dimethylformamide, N,N-dimethylacetamide or 1-methyl-2-pyrrolidone, in a temperature range of 0 to 100° C. within 1 to 24 hours. The precise reaction conditions depend on the corresponding reaction partners.

The reaction of compounds of formula V with an amine of formula VI is effected in accordance with process variant c). Halogen or aliphatic or aromatic sulphonyloxy groups are also suitable here as the leaving group X. The reaction is conveniently effected in a temperature range between 120 and 180° C. Phenol, ethoxyethanol, dimethylacetamide or 1-methyl-2-pyrrolidone is suitable as the solvent. The reaction duration can vary between 2 and 28 hours.

The reaction of aldehydes or ketones of formula VII with an amine of formula VI according to process variant d) is effected in a manner known per se. Conveniently, VII and VI are reacted in a solvent such as alcohol or toluene, with a water-separating agent such as e.g. molecular sieve optionally being added, and then a reducing agent such as a complex hydride, e.g. sodium borohydride, diborane or a metal, is then added thereto. VII and VI can also be reacted in the presence of a reducing agent such as hydrogen and a catalyst or with formic acid.

The conversion into a pharmaceutically usable salt is effected by adding an acid. Hydrochloric acid, methanesulphonic acid or acetic acid are especially preferred because of the physiological compatibility of the corresponding salts. Especially suitable solvents are conveniently: water, methanol, ethanol, isopropanol, diethyl ether, acetone, N,N-dimethylformamide or dioxan.

The intermediates required for variants a)–d) of the process can be prepared according to methods known per se. Examples 118–124 describe some possibilities for the preparation of the required intermediates.

The Schiff's bases of general formula II are conveniently obtained by reacting a diamine of formula III with an aldehyde of the formula

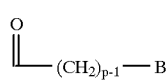

VIII

The reaction is conveniently carried out in an inert gas atmosphere at a temperature which lies between 20° C. and the boiling temperature of the solvent, for example of ethanol, toluene or dichloromethane. The reaction time can be between 1 and 24 hours, conveniently between 2 and 12 hours. The reaction water which is formed can be removed by water-binding agents such as a molecular sieve (preferably 4 Å), anhydrous sodium sulphate, by evaporation together with the solvent or by azeotropic distillation over a water separator.

As mentioned earlier, the $N_1$-arylalkyl-$N_2$-quinolin-4-yl-diamine derivatives of general formula I in accordance with the invention and their pharmaceutically usable salts have extremely valuable pharmacological properties.

In particular, they have a very good activity against malaria pathogens. Their activity is equally good against chloroquine-resistant strains of the pathogen as against chloroquine-sensitive strains. Accordingly, the novel compounds can also be used for the prophylaxis and cure of malaria even in those cases where the pathogen does not respond to chloroquine.

The activity of the novel compounds against not only chloroquine-resistant, but also chloroquine-sensitive malaria pathogens shows itself in a strong, in vitro measurable growth inhibition of various strains of the human-pathogenic *Plasmodium falciparum*, as set forth in Table 1 hereinafter. The ratio of the growth inhibition of a strain which is especially resistant to chloroquine and of a strain which is sensitive to chloroquine gives as the "resistance index" a measurement for the absence of a cross-resistance with chloroquine. Since, for all novel compounds the resistance index lies between 0.7 and 2.5, they inhibit the growth of sensitive as well as resistant strains of the malaria pathogen equally effectively. They are accordingly also suitable for the prophylaxis of a malaria disease and also for the treatment of a malaria disease even when chloroquine is ineffective. The good activity against malaria pathogens is also shown in animal experiments. The effective doses measured after oral and subcutaneous administration to mice infected with malaria pathogens are shown in Table 2 hereinafter.

Test method for the determination of the activity against *Plasmodium falciparum* in vitro The preparations are tested on intraerythrocytary stages of *Plasmodium falciparum* from asynchronous cultures according to the method of Desjardin et al. (Desjardins, R. E. et al: Quantitative assessment of antimalarial activity in vitro by a semiautomated microdilution technique. Antimicrob. Agents Chemother. 16, 710–718, (1979)).

The culture medium consists of RPMI 1640 with the addition of 25 mM HEPES, 25 mM NaHCO$_3$, 100 μg/ml neomycin and 105 human serum (A$^+$). Human-A$^+$ erythrocytes are used as the *Plasmodium falciparum* host cells. The parasites are maintained at 37° C. in an atmosphere of 3% O$_2$, 4% CO$_2$, 93% N$_2$ and 95% relative humidity.

In order to determine the activity, the preparations are dissolved in DMSO, pre-diluted in the culture medium to a suitable starting concentration and subsequently titrated-out on to microtitre plates in the 2nd stage over 6–7 steps. After the addition of the parasite culture (0.7% parasitemia in 2.5% erythrocyte suspension) the test plates are incubated under the conditions given above for 72 h. The parasite growth in the different preparation concentrations is determined using [G-$^3$H]-hypoxanthin incorporation compared to untreated control cultures on the same test plates. The 50% growth inhibition (IC$_{50}$) is calculated according to logit regression analysis from the resulting dosage-activity curve.

The preparations are tested on at least one chloroquine-resistant and one chloroquine-sensitive *Plasmodium falciparum* strain. Additional sensitive and resistant strains are included for further characterization.

Test method for the determination of the activity against *Plasmodium berghei* in vivo The preparations are tested on mice infected with malaria pathogens (*Plasmodium berghei*). Male albino mice (IBM:MORO(SPF), FUELLINSDORF) weighing about 25 g are used as the test animals. They are kept in climatized rooms at 21–22° C. in groups of 5 animals per cage. They receive ad libitum a diet feed with a low PABA content (NAFAG FUTTER " No. 9009 PAB-45, PABA content 45 mg/kg) and drinking water. On the first day of the test (D0) the test animals are infected with Plasmodium berghei (strain ANKA). For this there is used heparinized blood of a donor mouse with about 30% parasitemia, which is diluted with physiological saline such that it contains $10^8$ parasitized erythrocytes per ml. 0.2 ml of this suspension is injected intravenously (i.v.) into the mice to be treated and into the control mice. In untreated control animals the parasitemia normally reaches 30–40% on the third day after the infection (D+3) and the test animals die between days +5 and +7.

The substances to be tested are dissolved or suspended in distilled water or in a mixture of 7% Tween 80, 3% alcohol (96%) and water. Usually, 0.25 ml of this solution or suspension is administered once subcutaneously and perorally to groups of 5 test animals. Treatment is effected 24 hours after the infection. 10 control animals are treated in the same manner with solvent or suspension medium per test.

All substances are tested in a first test in a single dosage of 10 mg/kg. Only those substances which in this test (10 mg/kg) have shown a parasitaemia reduction of 90% are used for the titration. Suitable dilutions of the test substance can be used to obtain an accurate titration of the activity.

48 hours after the treatment (D+3) blood smears are prepared from all animals using blood from tail veins and are stained with giemsa. The average erythrocyte infection rate (parasitemiea in %) in the control groups as well as in the groups which have been treated with the test compounds is determined by counting under a microscope. The difference in the average values of the infection rates of control group (100%) and treated groups is calculated and expressed as a percentage reduction (GI%). The $ED_{50}$ or $ED_{90}$ is determined mathematically by means of the JMP programme (nonlinear fit). The $ED_{50}$ ($ED_{90}$) in mg/kg is that dose which after single administration reduces the average erythrocyte infection rate by 50% (90%) in comparison to the control group.

TABLE 1

Values measured in vitro ($IC_{50}$ values in ng/ml) for the growth inhibition of the human-pathogenenic *Plasmodium falciparum* strain NF54 as an example of a chloroquine-sensitive strain and of the human-pathogenenic *Plasmodium falciparum* K1 as an example of a chloroquine-resistant strain, as well as the "resistance index", the ratio of the $IC_{50}$ value for the chloroquine-resistant strain K1 and the $IC_{50}$ value for the chloroquine-sensitive strain NF54, as a measurement of the resistance to the test substance.

|  | $IC_{50}$ (ng/ml) for *P. falciparum* NF54 | $IC_{50}$ (ng/ml) for *P. falciparum* K1 | Resistance index |
| --- | --- | --- | --- |
| Chloroquine diphosphate | 6.7 | 95.0 | 14.2 |
| Amodiaquine | 2.5 | 3.5 | 1.4 |
| Example 1 | 12.6 | 17.5 | 1.4 |
| Example 2 | 7.1 | 14.8 | 2.1 |
| Example 3 | 13.7 | 18.3 | 1.3 |
| Example 4 | 9.1 | 8.8 | 1.0 |
| Example 5 | 49.3 | 57.2 | 1.2 |
| Example 6 | 10.3 | 14.5 | 1.4 |
| Example 7 | 24.0 | 34.9 | 1.5 |
| Example 8 | 16.1 | 18.9 | 1.2 |
| Example 9 | 13.2 | 16.7 | 1.3 |
| Example 10 | 51.7 | 50.4 | 1.0 |
| Example 11 | 29.3 | 48.0 | 1.6 |
| Example 12 | 84.7 | 197.0 | 2.3 |
| Example 13 | 2.7 | 16.1 | 6.0 |
| Example 14 | 4.8 | 28.4 | 5.9 |
| Example 15 | 4.3 | 14.7 | 3.4 |
| Example 16 | 2.0 | 17.0 | 8.5 |
| Example 17 | 6.4 | 17.4 | 2.8 |
| Example 18 | 5.5 | 21.0 | 3.8 |
| Example 19 | 4.9 | 14.3 | 2.9 |
| Example 20 | 4.4 | 10.8 | 2.5 |
| Example 21 | 5.1 | 9.3 | 1.8 |
| Example 22 | 11.6 | 18.9 | 1.6 |

TABLE 1-continued

Values measured in vitro ($IC_{50}$ values in ng/ml) for the growth inhibition of the human-pathogenenic *Plasmodium falciparum* strain NF54 as an example of a chloroquine-sensitive strain and of the human-pathogenenic *Plasmodium falciparum* K1 as an example of a chloroquine-resistant strain, as well as the "resistance index", the ratio of the $IC_{50}$ value for the chloroquine-resistant strain K1 and the $IC_{50}$ value for the chloroquine-sensitive strain NF54, as a measurement of the resistance to the test substance.

|  | $IC_{50}$ (ng/ml) for *P. falciparum* NF54 | $IC_{50}$ (ng/ml) for *P. falciparum* K1 | Resistance index |
| --- | --- | --- | --- |
| Chloroquine diphosphate | 6.7 | 95.0 | 14.2 |
| Amodiaquine | 2.5 | 3.5 | 1.4 |
| Example 23 | 29.6 | 32.5 | 1.1 |
| Example 24 | 7.9 | 13.2 | 1.7 |
| Example 25 | 17.3 | 12.9 | 0.7 |
| Example 26 | 26.3 | 37.3 | 1.4 |
| Example 27 | 16.0 | 23.3 | 1.5 |
| Example 28 | 4.0 | 10.7 | 2.7 |
| Example 29 | 7.7 | 16.2 | 2.1 |
| Example 30 | 6.7 | 11.4 | 1.7 |
| Example 31 | 6.5 | 9.9 | 1.5 |
| Example 32 | 7.6 | 14.7 | 1.9 |
| Example 33 | 6.3 | 7.1 | 1.1 |
| Example 34 | 7.2 | 15.0 | 2.1 |
| Example 35 | 6.4 | 13.3 | 2.1 |
| Example 36 | 16.2 | 20.7 | 1.3 |
| Example 37 | 11.0 | 11.0 | 1.0 |
| Example 38 | 10.1 | 15.1 | 1.5 |
| Example 39 | 7.8 | 10.3 | 1.3 |
| Example 40 | 3.6 | 7.1 | 2.0 |
| Example 41 | 13.5 | 18.7 | 1.4 |
| Example 42 | 8.7 | 12.6 | 1.4 |
| Example 43 | 16.0 | 18.1 | 1.1 |
| Example 44 | 10.8 | 15.4 | 1.4 |
| Example 45 | 12.3 | 12.5 | 1.0 |
| Example 46 | 10.1 | 12.6 | 1.2 |
| Example 47 | 9.4 | 13.6 | 1.4 |
| Example 48 | 12.3 | 15.9 | 1.3 |
| Example 49 | 8.2 | 12.4 | 1.5 |
| Example 50 | 14.2 | 14.3 | 1.0 |
| Example 51 | 12.3 | 9.1 | 0.7 |
| Example 52 | 34.6 | 55.6 | 1.6 |
| Example 53 | 15.9 | 14.9 | 0.9 |
| Example 54 | 19.3 | 29.0 | 1.5 |
| Example 55 | 7.8 | 14.5 | 1.9 |
| Example 56 | 31.3 | 53.7 | 1.7 |
| Example 57 | 21.7 | 28.2 | 1.3 |
| Example 58 | 29.3 | 69.0 | 2.4 |
| Example 59 | 166.4 | 185.7 | 1.1 |
| Example 60 | 7.7 | 12.2 | 1.6 |
| Example 61 | 12.7 | 11.2 | 0.9 |
| Example 62 | 50.8 | 64.2 | 1.3 |
| Example 63 | 10.1 | 14.6 | 1.4 |
| Example 64 | 35.7 | 82.3 | 2.3 |
| Example 65 | 9.9 | 25.3 | 2.6 |
| Example 66 | 5.6 | 10.5 | 1.9 |
| Example 67 | 9.1 | 23.0 | 2.5 |
| Example 68 | 5.9 | 14.6 | 2.5 |
| Example 69 | 3.7 | 4.6 | 1.2 |
| Example 70 | 3.8 | 6.6 | 1.7 |
| Example 71 | 7.1 | 9.3 | 1.3 |
| Example 72 | 11.6 | 11.2 | 1.0 |
| Example 73 | 15.0 | 19.0 | 1.3 |
| Example 74 | 23.3 | 14.5 | 0.6 |
| Example 75 | 25.0 | 18.0 | 0.7 |
| Example 76 | 7.2 | 6.1 | 0.8 |
| Example 77 | 96.6 | 63.2 | 0.7 |
| Example 79 | 4.1 | 7.7 | 1.9 |
| Example 80 | 8.9 | 18.4 | 2.1 |
| Example 81 | 4.3 | 9.7 | 2.3 |
| Example 82 | 5.7 | 8.5 | 1.5 |
| Example 83 | 8.6 | 5.9 | 0.7 |
| Example 84 | 6.9 | 7.8 | 1.1 |
| Example 85 | 4.6 | 3.9 | 0.8 |

TABLE 1-continued

Values measured in vitro ($IC_{50}$ values in ng/ml) for the growth inhibition of the human-pathogenenic *Plasmodium falciparum* strain NF54 as an example of a chloroquine-sensitive strain and of the human-pathogenenic *Plasmodium falciparum* K1 as an example of a chloroquine-resistant strain, as well as the "resistance index", the ratio of the $IC_{50}$ value for the chloroquine-resistant strain K1 and the $IC_{50}$ value for the chloroquine-sensitive strain NF54, as a measurement of the resistance to the test substance.

| | $IC_{50}$ (ng/ml) for *P. falciparum* NF54 | $IC_{50}$ (ng/ml) for *P. falciparum* K1 | Resistance index |
|---|---|---|---|
| Chloroquine diphosphate | 6.7 | 95.0 | 14.2 |
| Amodiaquine | 2.5 | 3.5 | 1.4 |
| Example 86 | 5.6 | 7.0 | 1.3 |
| Example 87 | 6.2 | 10.2 | 1.6 |
| Example 88 | 7.4 | 21.4 | 2.9 |
| Example 89 | 2.2 | 17.5 | 8.0 |
| Example 90 | 49.7 | 98.8 | 2.0 |
| Example 91 | 3.4 | 10.9 | 3.2 |
| Example 92 | 2.2 | 8.0 | 3.6 |
| Example 93 | 3.4 | 8.3 | 2.4 |
| Example 94 | 2.9 | 9.8 | 3.4 |
| Example 95 | 2.7 | 9.3 | 3.4 |
| Example 96 | 1.6 | 9.0 | 5.6 |
| Example 97 | 4.1 | 17.8 | 4.3 |
| Example 98 | 4.5 | 8.5 | 1.9 |
| Example 99 | 3.3 | 4.2 | 1.3 |
| Example 100 | 1.9 | 4.0 | 2.1 |
| Example 101 | 2.7 | 2.9 | 1.1 |
| Example 102 | 2.1 | 3.6 | 1.7 |
| Example 103 | 2.1 | 4.6 | 2.2 |
| Example 104 | 3.6 | 20.2 | 5.6 |
| Example 105 | 3.4 | 15.3 | 4.5 |
| Example 106 | 1.5 | 4.4 | 2.9 |
| Example 107 | 1.4 | 3.4 | 2.4 |
| Example 108 | 4.6 | 18.4 | 4.0 |
| Example 109 | 1.8 | 3.8 | 2.1 |
| Example 110 | 2.8 | 17.2 | 6.1 |
| Example 111 | 2.9 | 10.4 | 3.6 |
| Example 112 | 4.3 | 17.2 | 4.0 |
| Example 113 | 3.0 | 7.6 | 2.5 |
| Example 114 | 2.9 | 8.4 | 2.9 |

TABLE 2

Activity measured in vivo against *Plasmodium berghei* in mice: Gl% is the percentage reduction of the parasitemia after a single, peroral (po) or subcutaneous (sc) administered dose of 10 mg/kg of test substance; $ED_{50}$ is the effective perorally administered dose of test substance.

| | Growth inhibition in % after po administration | Growth inhibition in % after sc administration |
|---|---|---|
| Chloroquine diphosphate | 99.9 | 99.9 |
| Amodiaquine | 99.9 | 99.9 |
| Example 3 | 96.0 | 8.0 |
| Example 4 | 68.0 | 73.0 |
| Example 5 | 83.0 | 69.0 |
| Example 6 | 99.7 | 95.0 |
| Example 7 | 96.0 | 54.0 |
| Example 8 | 99.0 | 95.0 |
| Example 9 | 66.0 | 74.0 |
| Example 10 | 99.2 | 99.3 |
| Example 11 | 99.9 | 99.8 |
| Example 12 | 98.0 | 4.0 |
| Example 13 | 99.9 | 99.9 |
| Example 14 | 100.0 | 100.0 |
| Example 15 | 600 | 92.0 |
| Example 16 | 99.8 | 99.9 |
| Example 17 | 32.0 | 87.0 |
| Example 18 | 100.0 | 100.0 |
| Example 19 | 21.0 | toxic |
| Example 20 | 94.0 | 98.0 |
| Example 21 | 99.9 | 100.0 |
| Example 22 | 42.0 | 84.0 |
| Example 23 | 97.0 | 98.0 |
| Example 24 | 81.0 | 95.0 |
| Example 25 | 99.2 | 99.8 |
| Example 27 | 99.0 | 98.0 |
| Example 28 | 79.0 | 96.0 |
| Example 29 | 74.0 | 99.0 |
| Example 30 | 70.0 | 95.0 |
| Example 31 | 39.0 | 98.0 |
| Example 33 | 10.0 | 97.0 |
| Example 40 | 84.0 | 95.0 |
| Example 43 | 30.0 | 98.0 |
| Example 44 | 98.0 | 99.0 |
| Example 45 | 98.0 | 97.0 |
| Example 46 | 99.7 | 99.0 |
| Example 47 | 70.0 | 79.0 |
| Example 48 | 99.9 | 99.9 |
| Example 49 | 88.0 | 87.0 |
| Example 50 | 93.0 | 96.0 |
| Example 51 | 82.0 | 99.0 |
| Example 56 | 98.0 | 97.0 |
| Example 57 | 99.4 | 99.7 |
| Example 58 | 72.0 | 88.0 |
| Example 60 | 67.0 | 87.0 |
| Example 61 | 99.6 | 99.6 |
| Example 62 | 99.8 | 99.8 |
| Example 63 | 99.9 | 99.9 |
| Example 64 | 87.0 | 66.0 |
| Example 66 | 99.9 | 99.6 |
| Example 67 | 99.0 | 99.0 |
| Example 68 | 99.9 | 99.6 |
| Example 69 | 100.0 | 100.0 |
| Example 70 | 99.9 | 99.9 |
| Example 71 | 99.8 | 99.9 |
| Example 72 | 99.5 | 99.9 |
| Example 73 | 23.0 | 96.0 |
| Example 74 | 83.0 | 84.0 |
| Example 75 | 99.8 | 99.7 |
| Example 76 | 96.0 | 96.0 |
| Example 77 | 99.0 | 98.0 |
| Example 78 | 99.9 | 100.0 |
| Example 79 | 99.9 | 100.0 |
| Example 80 | 99.9 | 100.0 |
| Example 81 | 100.0 | 100.0 |
| Example 82 | 99.9 | 99.9 |
| Example 83 | 100.0 | 100.0 |
| Example 84 | 100.0 | 100.0 |
| Example 85 | 99.9 | 100.0 |
| Example 86 | 99.9 | 99.9 |
| Example 87 | 98.0 | 94.0 |
| Example 88 | 66.0 | 99.9 |
| Example 89 | 99.8 | 99.9 |
| Example 90 | 45.0 | 60.0 |
| Example 91 | 88.0 | 86.0 |
| Example 92 | 85.0 | 99.7 |
| Example 93 | 98.0 | 99.0 |
| Example 94 | 99.0 | 99.9 |
| Example 95 | 98.0 | 99.7 |
| Example 96 | 95.0 | 98.0 |
| Example 97 | 49.0 | 99.0 |
| Example 98 | 50.0 | 93.0 |

TABLE 2-continued

Activity measured in vivo against Plasmodium berghei in mice:
Gl% is the percentage reduction of the parasitemia after a single,
peroral (po) or subcutaneous (sc) administered dose of 10 mg/kg of
test substance; $ED_{50}$ is the effective perorally administered
dose of test substance.

|  | Growth inhibition in % after po administration | Growth inhibition in % after sc administration |
|---|---|---|
| Chloroquine diphosphate | 99.9 | 99.9 |
| Amodiaquine | 99.9 | 99.9 |
| Example 99 | 91.0 | 96.0 |
| Example 100 | 14.0 | 99.0 |
| Example 101 | 72.0 | 84.0 |
| Example 102 | 72.0 | 81.0 |
| Example 103 | 89.0 | 99.8 |
| Example 104 | 63.0 | 100.0 |
| Example 105 | 55.0 | 99.0 |
| Example 106 | 98.0 | 99.5 |
| Example 107 | 84.0 | 95.0 |
| Example 108 | 110.0 | 100.0 |
| Example 109 | 75.0 | 91.0 |
| Example 110 | 45.0 | 99.6 |
| Example 111 | 25.0 | 99.8 |
| Example 112 | 99.0 | 99.9 |
| Example 113 | 99.7 | 99.9 |
| Example 114 | 99.0 | 99.9 |

The compounds of formula I and the pharmaceutically acceptable acid addition salts of the compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions, or nasally.

The compounds of formula I and the pharmaceutically acceptable acid addition salts of the compounds of formula I can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active ingredient no carriers are, however, usually required in the case of soft gelatine capsules. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

Medicaments containing a compound of formula I or a pharmaceutically acceptable acid addition salt thereof and a therapeutically inert carrier are also an object of the present invention, as is a process for their manufacture which comprises bringing one or more compounds of formula I and/or pharmaceutically acceptable acid addition salts thereof into a galenical administration form together with one or more therapeutically inert carriers.

In accordance with the invention compounds of general formula I as well as their pharmaceutically acceptable acid addition salts can be used for the treatment or prevention of malaria and, respectively, for the production of corresponding medicaments. The dosage can vary within wide limits and will, of course, be fitted to the individual requirements in each particular case. In the case of oral administration the dosage lies in a range of about 10 mg to about 2.5 g per day of a compound of general formula I or the corresponding amount of a pharmaceutically acceptable acid addition salt thereof, although the upper limit can also be exceeded when this is found to be indicated.

In the following Examples, which illustrate the present invention but are not intended to limit its scope in any manner, all temperatures are given in degrees Celsius. The 250 MHz–$^1$H-NMR spectra are measured at room temperature; chemical shifts·δ(ppm) relative to δ(TMS)=0.0 ppm.

EXAMPLE 1

(2R)-$N_1$-(7-Chloro-quinolin-4-yl)-$N_2$-(4-dimethylamino-benzyl)-propane-1,2-diamine trihydrochloride

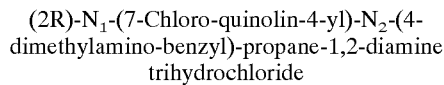

0.35 g of (2R)-$N_1$-(7-chloro-quinolin-4-yl)-propane-1,2-diamine (see Example 118) and 0.22g of 4-dimethylamino-benzaldehyde were boiled under reflux in 50 ml of ethanol overnight. After evaporation of the solvent the residue was again taken up in 20 ml of ethanol, 0.05 g of sodium borohydride was added thereto and the mixture was left to react at room temperature overnight. The excess sodium borohydride was then decomposed by the addition of 5 ml of glacial acetic acid and the solvent was evaporated. After the addition of 10 ml of methanol the mixture was again evaporated. Addition of methanol and evaporation were repeated again, whereafter the mixture was purified by chromatography on 30 g of silica gel with a mixture of dichloromethane and methanol in the ratio by volume 10:1. The product-containing fractions were combined and evaporated, and the residue was taken up in 5 ml of ethanol. After the addition of 5 ml of 3N isopropanolic hydrochloric acid the hydrochloride of the product precipitated and was recrystallized from ethanol/diethyl ether.

Yield: 0.5 g (70%) of colourless crystalline (2R)-$N_1$-(7-chloro-quinolin-4-yl)-$N_2$-(4-dimethylamino-benzyl)-propane-1,2-diamine trihydrochloride; m.p. 220° C.; ISP mass spectrum: peaks at 369 (M+H$^+$, 8%), 236 (58%), 134 (100%); $^1$H-NMR in DMSO-$d_6$, d (ppm): 1.44 (d, J=6.5 Hz, 3H), 2.92 (s, 6H), 3.58 (m, 1H), 3.85 (m, 1H), 4.0–4.5 (m, 3H), 6.95 (m, 2H), 7.07 (d, J=7 Hz, 1H), 7.50 (d, J=8 Hz, 2H), 7.80 (dd, J=2 and 9 Hz, 1H), 8.14 (d, J=2 Hz, 1H), 8.63 (m, 1H), 8.63 (m, 1H), 8.86 (d, J=9 Hz, 1H), 9.65 (m, 2H), 9.90 (m, 1H), 14.65 (br.s, 1H).

EXAMPLE 2

(2S)-$N_2$-(7-Chloro-quinolin-4-yl)-$N_1$-(4-dimethylamino-benzyl)-propane-1,2-diamine trihydrochloride

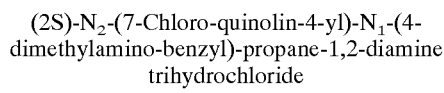

Analogously to Example 1, from 4-dimethylamino-benzaldehyde and (2S)-$N_2$-(7-chloro-quinolin-4-yl)-propane-1,2-diamine (see Example 119) there was obtained (2S)-$N_2$-(7-chloro-quinolin-4-yl)-$N_1$-(4-dimethylamino-benzyl)-propane-1,2-diamine trihydrochloride, m.p. 189° C. (from EtOH/Et$_2$O), in a yield of 57% of theory.

ISP mass spectrum: peaks at 369 (M+H$^+$, 20%), 236 (34%), 134 (100%); $^1$H-NMR in DMSO-$d_6$, d (ppm): 1.34

(d, J=6.5 Hz, 3H), 2.89 (s, 6H), 3.19 (m, 1H), 3.40 (m, 1H), 4.05 (m, 2H), 4.64 (m, 1H), 6.70 (d, J=8 Hz, 2H), 7.04 (d, J=7 Hz, 1H), 7.37 (d, J=8 Hz, 2H), 7.80 (dd, J=2 and 9 Hz, 1H), 8.09 (d, J=2 Hz, 1H), 8.61 (m, 1H), 8.84 (d, J=9 Hz, 1H), 9.28 (d, J=8 Hz, 1H), 9.35 (m, 1H), 9.55 (m, 1H), 14.45 (br.s, 1H).

EXAMPLE 3

$N_1$-(7-Chloro-quinolin-4-yl)-$N_2$-(3,4-dichloro-benzyl)-2-methyl-propane-1,2-diamine 1.25 g of $N_1$-(7-chloro-quinolin-4-yl)-2-methyl-propane-1,2-diamine and 0.88 g of 3,4-dichlorobenzaldehyde were heated under reflux in 10 ml of ethanol for 3 hours. In order to complete the reaction, the solvent was evaporated in a vacuum. The resulting Schiff's base was again taken up in 20 ml of ethanol and reduced to the amine by the addition of 0.19 g of sodium borohydride. Excess reducing agent was decomposed after 2 hours by the addition of 10 ml of glacial acetic acid. The turbid solution was then evaporated on a rotary evaporator. 10 ml of methanol were added to the residue and the mixture was again evaporated. Addition of methanol and evaporation were repeated twice. The evaporation residue was then taken up in 25 ml of water. The pH was adjusted to 10 by the addition of dilute sodium hydroxide solution, separating the product. The product was purified by recrystallization from 45 ml of ethyl acetate. Yield: 1.09 g (53%), m.p. 178–179° C.

$^1$H-NMR in DMSO-$d_6$, δ (ppm): 1.17(s, 6H), 3.24 (d, J=5 Hz, 2H), 3.69 (s, 2H), 6.59 (d, J=6 Hz, 1H), 6.70 (br. t, 1H), 7.35 (dd, J=2 Hz and 8 Hz, 1H), 7.46 (dd, J=2 Hz and 9 Hz, 1H), 7.52 (d, J=8 Hz, 1H), 7.62 (d, J=2 Hz, 1H), 7.79 (d, J=2 Hz, 1H), 8.26 (d, J=9 Hz, 1H), 8.40 (d, J=6 Hz, 1H).

The following products were obtained as free bases in an analogous manner using the corresponding aromatic aldehydes:

EXAMPLE 4

$N_1$-(7-Chloro-quinolin-4-yl)-$N_2$-(3-chloro-benzyl)-2-methyl-propane-1,2-diamine M.p.: 125–126° C. (from AcOEt); $^1$H-NMR in DMSO-$d_6$, δ (ppm): 1.18 (s, 6H), 3.24 (d, J=5 Hz, 2H), 3.69 (s, 2H), 6.60 (d, J=6 Hz, 1H), 6.71 (m, 1H), 7.45–7.74 (m, 3H), 7.43–7.49 (m, 2H), 7.80 (d, J=2 Hz, 1H), 8.27 (d, J=9 Hz, 1H), 8.41 (d, J=6 Hz, 1H).

EXAMPLE 5

$N_1$-(7-Chloro-quinolin-4-yl)-$N_2$-(2,4-dichloro-benzyl)-2-methyl-propane-1,2-diamine M.p.: 138–139° C. (from MeCN); $^1$H-NMR in DMSO-$d_6$, δ (ppm): 1.19 (s, 6H), 3.25 (d, J=5 Hz, 2H), 3.73 (s, 2H), 6.59 (d, J=6 Hz, 1H), 6.72 (m, 1H), 7.39 (dd, J=2 Hz and 8 Hz, 1H), 7.46 (dd, J=2 Hz and 9 Hz, 1H), 7.64 (d, J=8 Hz, 1H), 7.79 (d, J=2 Hz, 1H), 8.24 (d, J=9 Hz, 1H), 8.41 (d, J=6 Hz, 1H).

EXAMPLE 6

$N_1$-(7-Chloro-quinolin-4-yl)-$N_2$-(3-chloro-4-fluoro-benzyl)-2-methyl-propane-1,2-diamine M.p.: 164–165° C. (from MeCN); $^1$H-NMR in DMSO-$d_6$, δ (ppm): 1.17 (s, 6H), 3.24 (d, J=5 Hz, 2H), 3.67 (s, 2H), 6.60 (d, J=6 Hz, 1H), 6.69 (m, 1H), 7.25–7.38 (m, 2H), 7.46 (dd, J=2 Hz and 9 Hz, 1H), 7.56 (dd, J=2 Hz and 7 Hz, 1H), 7.80 (d, J=2 Hz, 1H), 8.27 (d, J=9 Hz, 1H), 8.41 (d, J=6 Hz, 1H).

EXAMPLE 7

$N_1$-(7-Chloro-quinolin-4-yl)-$N_2$-(4-chloro-3-trifluoromethyl-benzyl)-2-methyl-propane-1,2-diamine M.p.: 158–160° C. (from MeCN); $^1$H-NMR in DMSO-$d_6$, δ (ppm): 1.23 (s, 6H), 3.36 (s, 2H), 3.89 (s, 2H), 6.68 (d, J=6 Hz, 1H), 7.48 (dd, J=2 Hz and 9 Hz, 1H), 7.67 (d, J=8 Hz, 1H), 7.73 (m, 1H), 7.82 (d, J=2 Hz, 1H), 7.92 (m, 1H), 8.34 (d, J=9 Hz, 1H), 8.43 (d, J=6 Hz, 1H).

EXAMPLE 8

$N_1$-(7-Chloro-quinolin-4-yl)-$N_2$-(3-trifluoromethyl-benzyl)-2-methyl-propane-1,2-diamine M.p.: 156–157° C. (from MeCN); $^1$H-NMR in DMSO-$d_6$, δ (ppm): 1.19 (s, 6H), 3.25 (d, J=5 Hz, 2H), 3.78 (s, 2H), 6.61 (d, J=6 Hz, 1H), 7.43 (dd, J=2 Hz and 9 Hz, 1H), 7.45–7.74 (m, 3H), 7.80 (d, J=2 Hz, 1H), 8.27 (d, J=9 Hz, 1H), 8.41 (d, J=6 Hz, 1H).

EXAMPLE 9

$N_1$-(7-Chloro-quinolin-4-yl)-$N_2$-(4-trifluoromethyl-benzyl)-2-methyl-propane-1,2-diamine M.p.: 145–147° C. (from MeCN); $^1$H-NMR in DMSO-$d_6$, δ (ppm): 1.19 (s, 6H), 3.25 (d, J=5 Hz, 2H), 3.78 (s, 2H), 6.60 (d, J=6 Hz, 1H), 6.73 (m, 1H), 7.47 (dd, J=2 Hz and 9 Hz, 1H), 7.55–7.65 (m, 4H), 7.79 (d, J=2 Hz, 1H), 8.26 (d, J=9 Hz, 1H), 8.41 (d, J=6 Hz, 1H).

EXAMPLE 10

$N_1$-(7-Chloro-quinolin-4-yl)-$N_2$-(3,5-bis-trifluoromethyl-benzyl)-2-methyl-propane-1,2-diamine M.p.: 140–141° C. (from AcOEt); $^1$H-NMR in DMSO-$d_6$, δ (ppm): 1.19 (s, 6H), 2.65 (t, J=8 Hz, 1H), 3.26 (d, J=5 Hz, 2H), 3.89 (d, J=8 Hz, 2H), 6.62 (d, J=6 Hz, 1H), 6.73 (m, 1H), 7.41 (dd, J=2 Hz and 9 Hz, 1H), 7.79 (d, J=2 Hz, 1H), 7.91 (s, 1H), 8.06 (s, 2H), 8.26 (d, J=9 Hz, 1H), 8.39 (d, J=6 Hz, 1H).

EXAMPLE 11

$N_1$-(7-Chloro-quinolin-4-yl)-$N_2$-(pyridin-4-yl-methyl)-2-methyl-propane-1,2-diamine M.p.: 157–159° C. (from MeCN); $^1$H-NMR in DMSO-$d_6$, δ (ppm): 1.17 (s, 6H), 3.25 (m, 2H), 3.73 (s, 2H), 6.61 (d, J=6 Hz, 1H), 6.74 (m, 1H), 7.39 (d, J=7 Hz, 2H), 7.48 (dd, J=2 Hz and 9 Hz, 1H), 7.79 (d, J=2 Hz, 1H), 8.28 (d, J=9 Hz, 1H), 8.40 (d, J=6 Hz, 1H), 8.45 (d, J=7 Hz, 2H).

EXAMPLE 12

$N_1$-(7-Chloro-quinolin-4-yl)-$N_2$-(2,6-dichloro-benzyl)-2-methyl-propane-1,2-diamine M.p.: 154–155° C. (from MeCN); $^1$H-NMR in DMSO-$d_6$, δ (ppm): 1.25 (s, 6H), 2.0 (m, 1H), 3.25 (d, J=5 Hz, 2H), 3.87 (s, 2H), 6.59 (d, J=6 Hz, 1H), 6.61 (m, 1H), 7.25–7.50 (m, 4H), 7.81 (d, J=2 Hz, 1H), 8.20 (d, J=9 Hz, 1H), 8.42 (d, J=6 Hz, 1H).

EXAMPLE 13 cis-$N_1$-(7-Chloro-quinolin-4-yl)-$N_4$-phenethyl-cyclohexane-1,4-diamine dihydrochloride Analogously to Example 3 using phenylacetaldehyde. Yield: 10%, dec. >250° C.

EI mass spectrum: peaks at 380 ((M+H)$^+$, 100%), 276 (80%), 219 (50%); $^1$H-NMR in DMSO-d$_6$, δ (ppm): 1.96 (br, 9H), 3.08 (br, 4H), 3.32 (br, 1H), 4.10 (br, 1H), 8.93 (d, J=7 Hz, 1H), 7.32 (m, 5H), 7.80 (dd, J=2 and 9 Hz, 1H), 8.12 (d, J=2 Hz, 1H), 8.59 (d, J=7 Hz, 1H), 8.72 (d, 1H), 8.87 (d, J=9 Hz, 1H), 9.24 (br, 2H), 14.55 (br, 1H).

EXAMPLE 14 cis-$N_1$-(7-Chloro-quinolin-4-yl)-$N_4$-(2,4,6-trimethoxy-benzyl)-cyclohexane-1,4-diamine dihydrochloride Analogously to Example 3 using 2,4,6-trimethoxybenzaldehyde. Yield: 37% of white crystals (from methanol/diethyl ether), m.p. 195° C.

EI mass spectrum: peaks at 455 (M$^+$, 4%), 196 (28%), 181 (100%); $^1$H-NMR in DMSO-d$_6$, δ (ppm): 1.7–2.2 (m, 8H), 3.14 (br, 1H), 3.35 (s, 2H), 3.82 (s, 3H), 3.83 (2×s, 6H), 4.03 (br, 3H), 6.30 (s, 2H), 6.91 (d, J=6 Hz 1H), 7.76 (dd, J=2 and 9 Hz, 1H), 8.17 (d, J=2 Hz, 1H), 8.60 (br, 3H), 8.75 (d, J=6 Hz, 1H), 8.94 (d, J=9 Hz, 1H), 14.75(br, 1H).

EXAMPLE 15 cis-$N_1$-(7-Chloro-quinolin-4-yl)-$N_4$-(2,6-dichloro-benzyl)-cyclohexane-1,4-diamine dihydrochloride Analogously to Example 3 using 2,6-dichlorobenzaldehyde. Yield 43% of white crystals (from methanol/ether). M.p. >270° C.

ISP mass spectrum: peaks at 434(M$^+$, 100%), 436 ((M+2H)$^+$, 90%); $^1$H-NMR of the free base in CDCl$_3$, δ (ppm): 1.60–2.00 (m, 9H), 2.73 (br, 1H), 3.73 (br, 1H), 4.09 (s, 2H), 5.05 (d, 1H), 6.43 (d, J=5.5 Hz, 1H), 7.15 (m, 1H), 7.30 (s, 1H), 7.33 (s, 1H), 7.35 (dd, J=2 and 9 Hz, 1H), 7.62 (d, J=9 Hz, 1H), 7.95 (d, J=2 Hz, 1H), 8.51 (d, J=5.5 Hz, 1H).

EXAMPLE 16 cis-$N_1$-(7-Chloro-quinolin-4-yl)-$N_4$-(2,6-dimethoxy-benzyl)-cyclohexane-1,4-diamine dihydrochloride Analogously to Example 3 using 2,6-dimethoxybenzaldehyde. Yield 58% of beige crystals (from methanol/ether). M.p. 205° C.

ISP mass spectrum: peaks at 426 ((M+H)$^+$, 100%); $^1$H-NMR of beige crystals (from base in CDCl$_3$, δ (ppm): 1.60–2.00 (m, 8H), 2.70 (br, 2H), 3.75 (br, 1H), 3.82 (s, 6H), 3.94 (s, 2H), 5.20 (d, 1H), 6.41 (d, J=7 Hz, 1H), 6.52 (d, J=9 Hz, 2H), 7.17 (t, J=9 Hz, 1H), 7.35 (dd, J=2 and 10 Hz, 1H), 7.72 (d, J=10 Hz, 1H), 7.93 (d, J=2 Hz, 1H), 8.51 (d, J=7 Hz, 1H).

EXAMPLE 17 cis-$N_1$-(7-Chloro-quinolin-4-yl)-$N_4$-(2,3,6-trichloro-benzyl)-cyclohexane-1,4-diamine dihydrochloride Analogously to Example 3 using 2,3,6-trichlorobenzaldehyde. Yield 44% of white crystals (from methanol/ether). M.p. >270° C.

EI mass spectrum: peaks at 469 (M$^+$, 90%), 467(95%), 258(80%), 219(100%); $^1$H-NMR of the free base in CDCl$_3$, δ (ppm): 1.50–2.05 (m, 9H), 2.80 (br, 1H), 3.70 (br, 1H), 4.12 (s, 2H), 5.05 (d, 1H), 6.43 (d, J=5.5 Hz, 1H), 7.27 (d, J=8.5 Hz, 1H), 7.34 (d, J=8.5 Hz, 1H), 7.35 (dd, J=2 and 9 Hz, 1H), 7.63 (d, J=9 Hz, 1H), 7.95 (d, J=2 Hz, 1H), 8.51 (d, J=5.5 Hz, 1H).

EXAMPLE 18 cis-2-{[4-(7-Chloro-quinolin-4-ylamino)-cyclohexylamino]-methyl}-3,5-dimethoxy-phenol dihydrochloride Analogously to Example 3 using 4,6-dimethoxysalicylaldehyde. Yield 23% of beige crystals (from methanol/ether). M.p. 244° C.

ISP mass spectrum: peaks at 442 ((M+H)$^+$, 100%); $^1$H-NMR of the free base in CDCl$_3$ δ (ppm): 1.60–2.00 (m, 9H), 2.90 (br, 1H), 3.75 (s, 3H), 3.76 (s, 3H), 4.03 (s, 2H), 5.00 (d, 1H), 6.00 (d, J=2 Hz, 1H), 6.06 (d, J=2 Hz, 1H), 6.43 (d, J=7 Hz, 1H), 7.40 (dd, J=2 and 10 Hz, 1H), 7.70 (d, J=10 Hz, 1H), 7.95 (d, J=2 Hz, 1H), 8.50 (d, J=7 Hz, 1H).

EXAMPLE 19 cis-$N_1$-(7-Chloro-quinolin-4-yl)-$N_4$-(2,6-difluoro-benzyl)-cyclohexane-1,4-diamine dihydrochloride Analogously to Example 3 using 2,6-difluorobenzaldehyde. Yield 62% of white crystals (from methanol/ether). M.p. 225° C.

ISP mass spectrum: peaks at 402 ((M+H)$^+$, 100%), 276 (25%), 201 (75%); $^1$H-NMR of the free base in CDCl$_3$, δ (ppm): 1.50–2.00 (m, 9H), 2.75 (m, 1H), 3.70 (m, 1H), 3.92 (s, 2H), 5.05 (d, 1H), 6.42 (d, J=5.5 Hz, 1H), 6.89 (m, 2H), 7.20 (m, 1H), 7.35 (dd, J=2 and 9 Hz, 1H), 7.62 (d, J=9 Hz, 1H), 7.95 (d, J=2 Hz, 1H), 8.50 (d, J=5.5 Hz, 1H).

EXAMPLE 20 cis-$N_1$-(7-Chloro-quinolin-4-yl)-$N_4$-(3-phenyl-propyl)-cyclohexane-1,4-diamine dihydrochloride Analogously to Example 3 using 3-phenylpropionaldehyde. Yield 15% of white crystals (from methanol/ether). Dec. from 160° C.

ISP mass spectrum: peaks at 445 ((M+H)$^+$, 100%), 223 (½(M+2H)$^{2+}$; 25%); $^1$H-NMR of the dihydrochloride in d$_6$-DMSO δ (ppm): 1.64–2.25 (m, 10H), 2.69 (t, J=7 Hz, 2H), 2.90 (br, 2H), 3.24 (br, 1H), 4.08 (br, 1H), 6.90 (d, J=7 Hz, 1H), 7.26 (m, 5H), 7.75 (dd, J=2 and 9 Hz, 1H), 8.16 (d, J=2 Hz, 1H), 8.58 (d, J=7 Hz, 1H), 8.75 (d, br, 2H), 8.88 (d, J=9 Hz, 1H), 9.18 (br, 2H), 14.4 (br, 1H).

EXAMPLE 21 cis-$N_1$-(7-Chloro-quinolin-4-yl)-$N_4$-(4-methoxy-benzyl)-cyclohexane-1,4-diamine dihydrochloride Analogously to Example 3 using anisaldehyde. Yield 34% of white crystals (from methanol/ether). M.p. >185° C.

EI mass spectrum: peaks at 395 (M$^+$, 26%), 260 (65%), 219 (34%), 121 (100%); $^1$H-NMR of the dihydrochloride in d$_6$-DMSO δ (ppm): 1.66–2.25 (m, 8H), 3.18 (br, 1H), 3.77 (s, 3H), 4.11 (br, 3H), 6.90 (d, J=7 Hz, 1H), 6.98 (d, J=8.6 Hz, 2H), 7.55 (d, J=8.6 Hz, 2H), 7.78 (dd, J=2 and 9 Hz, 1H), 8.11 (d, J=2 Hz, 1H), 8.58 (d, J=7 Hz, 1H), 8.64 (d, br, 2H), 8.87 (d, J=9 Hz, 1H), 9.32 (br, 2H), 14.5 (br, 1H).

EXAMPLE 22 cis-$N_1$-(2-Chloro-6-nitro-benzyl)-$N_4$-(7-chloro-quinolin-4-yl)-cyclohexane-1,4-diamine dihydrochloride Analogously to Example 3 using 2-chloro-6-nitrobenzaldehyde. Yield 23% of white crystals (from methanol/ether). M.p. >260° C.

ISP mass spectrum: peaks at 445 ((M+H)$^+$, 100%), 223 (½(M+2H)$^{2+}$; 25%); $^1$H-NMR of the free base in CDCl$_3$, δ (ppm): 1.50–2.00 (m, 9H), 2.85 (m, 1H), 3.71 (m, 1H), 4.06 (s, 2H), 5.03 (d, 1H), 6.43 (d, J=5.5 Hz, 1H), 7.37 (m, 2H), 7.68 (m, 3H), 7.95 (d, J=2 Hz, 1H), 8.51 (d, J=5.5 Hz, 1H).

EXAMPLE 23

N$_1$-(7-Chloro-quinolin-4-yl)-N$_2$-(3,5-dichloro-benzyl)-2-methylpropane-1,2-diamine dihydrochloride 1.25 g of N$_1$-(7-chloro-quinolin-4-yl)-2-methyl-propane-1,2-diamine and 0.88 g of 3,5-dichlorobenzaldehyde were heated under reflux in 10 ml of ethanol for 3 hours. The solvent was evaporated in a vacuum in order to complete the reaction. The resulting Schiff's base was again taken up in 10 ml of ethanol and reduced to the amine by the addition of 0.19 g of sodium borohydride. Excess reducing agent was decomposed after 3 hours by the addition of 10 ml of glacial acetic acid. The turbid solution was then evaporated on a rotary evaporator. The residue was taken up in 10 ml of methanol, which was again evaporated. Addition of methanol and evaporation were repeated twice. The evaporation residue was then dissolved in 15 ml of hot methanol. After the addition of 3.6 ml of 3N isopropanolic hydrochloric acid the hydrochloride of the product crystallized upon cooling. The crude salt (1.1 g) was purified by recrystallization from 30 ml of methanol. Yield: 0.63 g (26%), m.p. >250° C.; $^1$H-NMR in DMSO-d$_6$, δ (ppm): 1.50 (s, 6H), 4.03 (br.s, 2H), 4.35 (m, 2H), 7.27 (d, J=7 Hz, 1H), 7.69 (m, 1H), 7.82 (dd, J=2 Hz and 9 Hz), 7.89 (m, 2H), 8.11 (d, J=2 Hz, 1H), 8.68 (d, J=7 Hz, 1H), 8.99 (d, J=9 Hz, 1H), 9.65 (br., 1H), 9.8 (m, 2H), 14.5 (br.s, 1H).

The hydrochlorides of the following products were obtained in an analogous manner using the corresponding benzaldehydes:

EXAMPLE 24

N$_1$-(7-Chloro-quinolin-4-yl)-N$_2$-(benzyl)-2-methyl-propane-1,2-diamine dihydrochloride M.p.: >250° C. (from i-PrOH); EI mass spectrum: fragments at 192 (16%), 148 (100%), 91 (96%); $^1$H-NMR in DMSO-d$_6$, δ (ppm): 1.53 (s, 6H), 4.06 (m, 2H), 4.29 (m, 2H), 7.28 (d, J=7 Hz, 1H), 7.40–7.45 (m, 3H), 7.70–7.82 (m, 3H), 8.17 (d, J=2 Hz, 1H), 8.67 (d, J=7 Hz, 1H), 9.03 (d, J=9 Hz, 1H), 9.70 (m, 3H), 14.65 (br.s, 1H).

EXAMPLE 25

N$_1$-(7-Chloro-quinolin-4-yl)-N$_2$-(4-chloro-benzyl)-2-methyl-propane-1,2-diamine dihydrochloride M.p.: >250° C. (from i-PrOH); EI mass spectrum: fragments at 192 (43%), 182 (75%), 125 (100%); $^1$H-NMR in DMSO-d$_6$, δ (ppm): 1.52 (s, 6H), 4.05 (m, 2H), 4.30 (m, 2H), 7.28 (d, J=7 Hz, 1H), 7.51 (d, J=8.5 Hz, 2H), 7.75–7.80 (m, 3H), 7.70–7.82 (m, 3H), 8.15 (d, J=2 Hz, 1H), 8.67 (d, J=7 Hz, 1H), 9.02 (d, J=9 Hz, 1H), 9.5–10.0 (m, 3H), 14.30 (br.s, 1H).

EXAMPLE 26

N$_1$-(7-Chloro-quinolin-4-yl)-N$_2$-(2,3-dichloro-benzyl)-2-methyl-propane-1,2-diamine dihydrochloride M.p.: >250° C. (from i-PrOH); $^1$H-NMR in DMSO-d$_6$, δ (ppm): 1.55 (s, 6H), 4.08 (m, 2H), 4.46 (m, 2H), 7.28 (d, J=7.5 Hz, 1H), 7.48 (t, J=8 Hz, 1H), 7.70–7.85 (m, 2H), 8.02 (dd, J=2 Hz and 8 Hz, 1H), 8.20 (d, J=2 Hz, 1H), 8.70 (d, J=7.5 Hz, 1H), 9.07 (d, J=9 Hz, 1H), 9.70 (m, 1H), 10.00 (m, 2H), 14.90 (br.s, 1H).

EXAMPLE 27

N$_1$-(7-Chloro-quinolin-4-yl)-N$_2$-(4-chloro-3-fluoro-benzyl)-2-methyl-propane-1,2-diamine dihydrochloride M.p.: >250° C. (from MeOH); $^1$H-NMR in DMSO-d$_6$, δ (ppm): 1.50 (s, 6H), 4.04 (m, 2H), 4.34 (m, 2H), 7.28 (d, J=7 Hz, 1H), 7.60 (dd, J=2 Hz and 8 Hz, 1H), 7.70 (t, J=8 Hz, 1H), 7.82 (dd, J=2 Hz and 9 Hz, 1H), 7.90 (dd, J=2 Hz and 10 Hz), 8.10 (d, J=2 Hz, 1H), 8.68 (d, J=7 Hz, 1H), 8.98 (d, J=9 Hz, 1H), 9.6 (m, 1H), 9.85 (m, 2H), 14.5 (br.s, 1H).

EXAMPLE 28

N$_1$-(7-Chloro-quinolin-4-yl)-N$_2$-(2-hydroxybenzyl)-2-methyl-propane-1,2-diamine diacetate 1.25 g of N$_1$-(7-chloro-quinolin-4-yl)-2-methyl-propane-1,2-diamine and 0.54 g of salicylaldehyde were stirred under reflux overnight in the presence of 1.25 g of molecular sieve (E. Merck, 3 Å). Thereafter, the mixture was filtered and the solvent was evaporated. From a small amount of diethyl ether and ethyl acetate there was obtained a crystalline product which was again taken up in 20 ml of ethanol. After the addition of 0.19 g of sodium borohydride the mixture was left to react overnight, thereafter 5 ml of glacial acetic acid were added thereto and the mixture was evaporated to dryness. After the addition of 10 ml of methanol the mixture was again evaporated. Addition of methanol and evaporation were repeated twice. The residue was then crystallized from 10 ml of ethanol. 0.9 g (40%) of colourless crystalline product of m.p. 150° C. was obtained.

ISP-mass spectrum: peaks at 356 (M+H$^+$, 65%), 250 (80%), 107 (100%); $^1$H-NMR in DMSO-d$_6$, δ (ppm): 1.20 (s, 6H), 1.90 (s, 6H), 3.33 (s, 2H), 3.84 (s, 2H), 6.63–6.74 (m, 3H), 7.03–7.13 (m, 2H), 7.47 (dd, J=2 and 9 Hz, 1H), 7.80 (d, J=2 Hz, 1H), 8.31 (d, J=9 Hz, 1H), 8.41 (d, J=7 Hz, 1H).

EXAMPLE 29

N$_1$-(7-Chloro-quinolin-4-yl)-N$_2$-(2-hydroxy-4-methoxy-benzyl)-2-methyl-propane-1,2-diamine dihydrochloride 1.25 g of N$_1$-(7-chloro-quinolin-4-yl)-2-methyl-propane-1,2-diamine and 0.76 g of 2-hydroxy-4-methoxy-benzaldehyde were stirred under reflux overnight in 20 ml of ethanol in the presence of 1.25 g of molecular sieve (E. Merck, 3 Å). The mixture was filtered, the solvent was evaporated and the residue was again taken up in 20 ml of ethanol. After the addition of 0.19 g of sodium borohydride the mixture was stirred at room temperature for 6 hours, thereafter 5 ml of glacial acetic acid were added thereto and the mixture was evaporated to dryness. 10 ml of methanol were added to the residue and the mixture was again evaporated. Addition of methanol and evaporation were repeated twice. Finally, the residue was taken up in 10 ml of hot ethanol, 10 ml of 3N isopropanolic hydrochloric acid were added thereto and the product was left to crystallize out as the dihydrochloride. Yield 1.8 g (78%) of colourless crystalline powder, m.p. 220° C.

ISP mass spectrum: peaks at 386 (M+H$^+$, 20%), 250 (70%), 137 (100%); $^1$H-NMR in DMSO-d$_6$, δ (ppm): 1.48

(s, 6H), 3.71 (s, 3H), 4.02 (m, 2H), 4.10 (m, 2H), 6.44 (dd, J=2 and 8 Hz, 1H), 6.59 (d, J=2 Hz, 1H), 7.22 (d, J=7 Hz, 1H), 7.47 (d, J=8 Hz, 1H), 7.80 (dd, J=2 Hz and 9 Hz, 1H), 8.21 (d, J=2 Hz, 1H), 8.67 (d, J=7 Hz, 1H), 9.02 (d, J=9 Hz, 1H), 9.30 (m, 2H), 9.57 (m, 1H), 10.40 (m, 1H), 14.94 (br.s, 1H).

The hydrochlorides of the following products were obtained in an analogous manner using the corresponding aromatic aldehydes:

EXAMPLE 30

$N_1$-(7-Chloro-quinolin-4-yl)-$N_2$-(2-hydroxy-3-methoxy-benzyl)-2-methyl-propane-1,2-diamine dihydrochloride Yield 82%, m.p.: 210–212° C. (from EtOH/i-PrOH); ISP mass spectrum: peaks at 386 (M+H$^+$, 44%), 250 (100%); $^1$H-NMR in DMSO-d$_6$, δ (ppm): 1.49 (s, 6H), 3.83 (s, 3H), 4.03 (m, 2H), 4.20 (m, 2H), 6.83 (t, J=8 Hz, 1H), 7.03 (dd, J=1.5 and 8 Hz, 1H), 7.23 (m, 2H), 7.80 (dd, J=2 Hz and 9 Hz, 1H), 8.20 (d, J=2 Hz, 1H), 8.66 (d, J=7 Hz, 1H), 9.01 (d, J=9 Hz, 1H), 9.36 (m, 3H), 9.59 (m, 1H), 14.65 (br.s, 1H).

EXAMPLE 31

$N_1$-(7-Chloro-quinolin-4-yl)-$N_2$-(2-hydroxy-5-methoxy-benzyl)-2-methyl-propane-1,2-diamine dihydrochloride Yield 44%, m.p.: >250° C. (from EtOH/i-PrOH); ISP mass spectrum: peaks at 386 (M+H$^+$, 67%), 250 (100%); $^1$H-NMR in DMSO-d$_6$, δ (ppm): 1.50 (s, 6H), 3.71 (s, 3H), 4.03 (m, 2H), 4.17 (m, 2H), 6.80–6.94 (m, 2H), 7.23–7.29 (m, 2H), 7.80 (dd, J=2 Hz and 9 Hz, 1H), 8.14 (d, J=2 Hz, 1H), 8.68 (d, J=7 Hz, 1H), 8.97 (d, J=9 Hz, 1H), 9.34 (m, 2H), 9.50 (m, 1H), 9.75 (m, 1H), 14.65 (br.s, 1H).

EXAMPLE 32

$N_1$-(7-Chloro-quinolin-4-yl)-$N_2$-(3-hydroxy-benzyl)-2-methyl-propane-1,2-diamine dihydrochloride Yield 56%, m.p.: >250° C. (from EtOH/i-PrOH); ISP mass spectrum: peaks at 356 (M+H$^+$); $^1$H-NMR in DMSO-d$_6$, δ (ppm): 1.50 (s, 6H), 4.04 (m, 2H), 4.18 (m, 2H), 6.83 (m, 1H), 7.04–7.30 (m, 4H), 7.81 (dd, J=2 Hz and 9 Hz, 1H), 8.19 (d, J=2 Hz, 1H), 8.67 (d, J=7 Hz, 1H), 9.02 (d, J=9 Hz, 1H), 9.65 (m, 3H), 9.74 (s, 1H), 14.80 (br.s, 1H).

EXAMPLE 33

$N_1$-(7-Chloro-quinolin-4-yl)-$N_2$-(4-hydroxy-3-methoxy-benzyl)-2-methyl-propane-1,2-diamine dihydrochloride Yield 68%, m.p.: >250° C. (from EtOH/i-PrOH); ISP mass spectrum: peaks at 386 (M+H$^+$, 100%), 250 (52%); $^1$H-NMR in DMSO-d$_6$, δ (ppm): 1.50 (s, 6H), 3.81 (s, 3H), 4.04 (m, 2H), 4.17 (m, 2H), 6.80 (d, J=8 Hz, 1H), 7.04 (dd, J=2 and 8 Hz, 1H), 7.27 (d, J=7 Hz, 1H), 7.50 (d, J=2, 1H), 7.79 (dd, J=2 Hz and 9 Hz, 1H), 8.18 (d, J=2 Hz, 1H), 8.66 (d, J=7 Hz, 1H), 9.04 (d, J=9 Hz, 1H), 9.60 (m, 3H), 14.83 (br.s, 1H).

EXAMPLE 34

$N_1$-(7-Chloro-quinolin-4-yl)-$N_2$-(2-methoxy-benzyl)-2-methyl-propane-1,2-diamine dihydrochloride Yield 68%, m.p.: >250° C. (from EtOH/i-PrOH); ISP mass spectrum: peaks at 370 (M+H$^+$, 100%), 250 (75%); $^1$H-NMR in DMSO-d$_6$, δ (ppm): 1.50 (s, 6H), 3.82 (s, 3H), 4.05 (m, 2H), 4.20 (m, 2H), 7.00 (t, J=8 Hz, 1H), 7.09 (d, J=8 Hz, 1H), 7.26 (d, J=7 Hz, 1H), 7.43 (dt, J=2 and 8 Hz, 1H), 7.59 (dd, J=2 and 8 Hz, 1H), 7.80 (dd, J=2 Hz and 9 Hz, 1H), 8.20 (d, J=2 Hz, 1H), 8.68 (d, J=7 Hz, 1H), 9.07 (d, J=9 Hz, 1H), 9.45 (m, 2H), 9.65 (m, 1H), 14.83 (br.s, 1H).

EXAMPLE 35

$N_1$-(7-Chloro-quinolin-4-yl)-$N_2$-(4-methoxy-benzyl)-2-methyl-propane-1,2-diamine dihydrochloride M.p.: >250° C. (from EtOH); $^1$H-NMR in DMSO-d$_6$, δ (ppm): 1.50 (s, 6H), 3.77 (s, 3H), 4.03 (m, 2H), 4.22 (m, 2H), 6.99 (d, J=9 Hz, 2H), 7.27 (d, J=7 Hz, 2H), 7.64 (d, J=9 Hz, 2H), 7.81 (dd, J=2 Hz and 9 Hz), 8.14 (d, J=2 Hz, 1H), 8.68 (d, J=7 Hz, 1H), 9.01 (d, J=9 Hz, 1H), 9.63 (m, 3H), 14.65 (br.s, 1H).

EXAMPLE 36

$N_1$-(7-Chloro-quinolin-4-yl)-$N_2$-(2,3-dimethoxy-benzyl)-2-methyl-propane-1,2-diamine dihydrochloride M.p.: >250° C. (from EtOH/i-PrOH); $^1$H-NMR in DMSO-d$_6$, δ (ppm): 1.50 (s, 6H), 3.83 (s, 3H), 3.84 (s, 3H), 4.04 (m, 2H), 4.22 (m, 2H), 7.14 (d, J=5 Hz, 2H), 7.25 (d, J=7 Hz, 1H), 7.35 (t, J=5 Hz, 1H), 7.81 (dd, J=2 Hz and 9 Hz, 1H), 8.14 (d, J=2 Hz, 1H), 8.69 (d, J=7 Hz, 1H), 9.00 (d, J=9 Hz, 1H), 9.54 (m, 3H), 14.65 (br.s, 1H).

EXAMPLE 37

$N_1$-(7-Chloro-quinolin-4-yl)-$N_2$-(2,4-dimethoxy-benzyl)-2-methyl-propane-1,2-diamine dihydrochloride Yield 42%, m.p.: >250°C. (from EtOH/i-PrOH); EI mass spectrum: fragments at 301, 208, 191, 151 (100%); $^1$H-NMR in DMSO-d$_6$, δ (ppm): 1.49 (s, 6H), 3.79 (s, 3H), 3.80 (s, 3H), 4.02 (m, 2H), 4.11 (m, 2H), 6.54–6.63 (m, 2H), 7.24 (d, J=7 Hz, 1H), 7.52 (d, J=8 Hz, 1H), 7.80 (dd, J=2 Hz and 9 Hz, 1H), 8.20 (d, J=2 Hz, 1H), 8.67 (d, J=7 Hz, 1H), 9.08 (d, J=9 Hz, 1H), 9.35 (m, 2H), 9.63 (m, 1H), 14.90 (br.s, 1H).

EXAMPLE 38

$N_1$-(7-Chloro-quinolin-4-yl)-$N_2$-(2,5-dimethoxy-benzyl)-2-methyl-propane-1,2-diamine dihydrochloride Yield 72%, m.p.: >250° C. (from EtOH/i-PrOH); ISP mass spectrum: peaks at 400 (M+H$^+$, 100%), 384 (27%), 250 (85%); $^1$H-NMR in DMSO-d$_6$, δ (ppm): 1.50 (s, 6H), 3.74 (s, 3H), 3.77 (s, 3H), 4.03 (m, 2H), 4.18 (m, 2H), 6.94–7.04 (m, 2H), 7.25 (d, J=7 Hz, 1H), 7.35 (d, J=2 Hz, 1H), 7.79 (dd, J=2 Hz and 9 Hz, 1H), 8.20 (d, J=2 Hz, 1H), 8.68 (d, J=7Hz, 1H), 9.06 (d, J=9 Hz, 1H), 9.60 (m, 3H), 14.80 (br.s, 1H).

EXAMPLE 39

$N_1$-(7-Chloro-quinolin-4-yl)-$N_2$-(3,4-dimethoxy-benzyl)-2-methyl-propane-1,2-diamine dihydrochloride Yield 72%, m.p.: >250° C. (from EtOH/i-PrOH); $^1$H-NMR in DMSO-d$_6$, δ (ppm): 1.53 (s, 6H), 3.76 (s, 3H), 3.81 (s, 3H), 4.06 (m, 2H), 4.20 (m, 2H), 6.97 (d, J=8.5 Hz, 1H), 7.19 (dd, J=2 Hz and 8.5 Hz, 1H), 7.28 (d, J=7.5 Hz, 1H), 7.56 (d, J=2 Hz, 1H), 7.76 (dd, J=2 and 8.5 Hz, 1H), 8.23 (d, J=2 Hz, 1H), 8.65 (d, J=7.5 Hz, 1H), 9.09 (d, J=8.5 Hz, 1H), 9.75 (m, 3H), 15.00 (br.s, 1H).

EXAMPLE 40

$N_1$-(7-Chloro-quinolin-4-yl)-$N_2$-(3,5-dimethoxy-benzyl)-2-methyl-propane-1,2-diamine dihydrochloride M.p.: >250° C. (from EtOH); $^1$H-NMR in DMSO-$d_6$, δ (ppm): 1.51 (s, 6H), 3.78 (s, 6H), 4.05 (m, 2H), 4.22 (m, 2H), 6.51 (m, 1H), 6.99 (m, 2H), 7.28 (d, J=7 Hz, 1H), 7.81 (dd, J=2 Hz and 9 Hz), 8.14 (d, J=2 Hz, 1H) 8.68 (d, J=7 Hz, 1H), 9.01 (d, J=9 Hz, 1H), 9.67 (m, 3H), 14.65 (br.s, 1H).

EXAMPLE 41

$N_1$-(7-Chloro-quinolin-4-yl)-$N_2$-(3,4,5-trimethoxy-benzyl)-2-methyl-propane-1,2-diamine dihydrochloride Yield 60%, m.p.: >250° C. (from EtOH/i-PrOH); ISP mass spectrum: peaks at 430 (M+H$^+$); $^1$H-NMR in DMSO-$d_6$, δ (ppm): 1.51 (s, 6H), 3.65 (s, 3H), 3.82 (s, 6H), 4.05 (m, 2H), 4.22 (m, 2H), 7.18 (s, 2H), 7.28 (d, J=7 Hz, 1H), 7.80 (dd, J=2 Hz and 9 Hz, 1H), 8.10 (d, J=2 Hz, 1H), 8.66 (d, J=7 Hz, 1H), 8.97 (d, J=9 Hz, 1H), 9.64 (m, 3H), 14.55 (br.s, 1H).

EXAMPLE 42

$N_1$-(7-Chloro-quinolin-4-yl)-$N_2$-benzo[1,3]dioxol-5-ylmethyl-2-methyl-propane-1,2-diamine dihydrochloride Yield 61%, m.p.: >250° C. (from EtOH/i-PrOH); ISP mass spectrum: peaks at 384 (M+H$^+$), 250 (79%); $^1$H-NMR in DMSO-$d_6$, δ (ppm): 1.49 (s, 6H), 4.04 (m, 2H), 4.23 (m, 2H), 6.98 (d, J=7 Hz, 1H), 7.17 (dd, J=2 Hz and 7 Hz, 1H), 7.30 (d, J=7 Hz, 1H), 7.39 (d, J=2 Hz, 1H), 7.80 (dd, J=2 Hz and 9 Hz, 1H), 8.14 (d, J=2 Hz, 1H), 8.67 (d, J=7 Hz, 1H), 9.00 (d, J=9 Hz, 1H), 9.63 (m, 3H), 14.58 (br.s 1H).

EXAMPLE 43

$N_1$-(7-Chloro-quinolin-4-yl)-$N_2$-(4-phenoxy-benzyl)-2-methyl-propane-1,2-diamine dihydrochloride M.p.: >250° C. (from MeOH); $^1$H-NMR in DMSO-$d_6$, δ (ppm): 1.51 (s, 6H), 4.05 (m, 2H), 4.28 (m, 2H), 7.00–7.08 (m, 4H), 7.15–7.21 (m, 1H), 7.28 (d, J=7.5 Hz, 2H), 7.39–7.46 (m, 2 H), 7.74 (d, J=9 Hz, 2H), 7.81 (dd, J=2 Hz and 9 Hz), 8.14 (d, J=2 Hz, 1H), 8.69 (d, J=7.5 Hz, 1H), 9.01 (d, J=9 Hz, 1H), 9.66 (m, 3H), 14.65 (br.s, 1H).

EXAMPLE 44

$N_1$-(7-Chloro-quinolin-4-yl)-$N_2$-(4-methylsulphanyl-benzyl)-2-methyl-propane-1,2-diamine dihydrochloride M.p.: >250° C. (from MeOH); $^1$H-NMR in DMSO-$d_6$, δ (ppm): 1.50 (s, 6H), 2.50 (s, 3H), 4.03 (m, 2H), 4.25 (m, 2H), 7.28 (d, J=7 Hz, 1H), 7.32 (d, J=9.5 Hz, 2H), 7.65 (d, J=9.5 Hz, 2H), 7.80 (dd, J=2 Hz and 9 Hz, 1H), 8.11 (d, J=2 Hz, 1H), 8.69 (d, J=7 Hz, 1H), 8.98 (d, J=9 Hz, 1H), 9.6 (m, 3H), 14.50 (br.s, 1H).

EXAMPLE 45

$N_1$-(7-Chloro-quinolin-4-yl)-$N_2$-(4-dimethylamino-benzyl)-2-methyl-propane-1,2-diamine dihydrochloride M.p.: >250° C. (from MeOH); $^1$H-NMR in DMSO-$d_6$, δ (ppm): 1.49 (s, 6H), 2.91 (s, 6H), 4.01 (m, 2H), 4.13 (m, 2H), 6.74 (d, J=9 Hz, 2H), 7.25 (d, J=7.5 Hz, 1H), 7.48 (d, J=9 Hz, 2H), 7.82 (dd, J=2 Hz and 9 Hz, 1H), 8.12 (d, J=2 Hz, 1H), 8.68 (d, J=7.5 Hz, 1H), 8.98 (d, J=9 Hz, 1H), 9.45 (m, 2H), 9.55 (m, 1H), 14.60 (br.s, 1H).

EXAMPLE 46

$N_1$-(7-Chloro-quinolin-4-yl)-$N_2$-(4-diethylamino-benzyl)-2-methyl-propane-1,2-diamine trihydrochloride Yield 21%, m.p. >250° C. (from EtOH); ISP mass spectrum: peaks at 411 (M+H$^+$, 5%) 250 (24%), 233 (16%), 206 ([M+2H$^+$]/2, 100%), 162 (98%); $^1$H-NMR in DMSO-$d_6$, δ (ppm): 1.05 (t, J=7 Hz, 6H), 1.51 (s, 6H), 3.44 (q, J=7 Hz, 4H), 4.05 (m, 2H), 4.35 (m, 2H), 7.28 (d, J=7.5 Hz, 1H), 7.82 (dd, J=2 Hz and 9 Hz, 1H), 7.95, (m, 2H), 8.12 (d, J=2 Hz, 1H), 8.68 (d, J=7.5 Hz, 1H), 9.00 (d, J=9 Hz, 1H), 9.65 (m, 1H), 9.85 (m, 1H), 14.58 (br.s, 1H).

EXAMPLE 47

$N_1$-(7-Chloro-quinolin-4-yl)-$N_2$-(4-nitro-benzyl)-2-methy -propane-1,2-diamine dihydrochloride M.p.: >250° C. (from EtOH/i-Pr ether; $^1$H-NMR in DMSO-$d_6$, δ (ppm): 1.54 (s, 6H), 4.08 (m, 2H), 4.48 (m, 2H), 7.30 (d, J=7 Hz, 2H), 7.81 (dd, J=2 Hz and 9 Hz), 8.04 (d, J=8.5 Hz, 2H), 8.13 (d, J=2 Hz, 1H), 8.30 (d, J=8.5 Hz, 2H), 8.68 (d, J=7 Hz, 1H), 9.00 (d, J=9 Hz, 1H), 9.66 (m, 1H), 10.0 (m, 2H), 14.65 (br.s, 1H).

EXAMPLE 48

$N_1$-(7-Chloro-quinolin-4-yl)-$N_2$-(3-cyano-benzyl)-2-methyl-propane-1,2-diamine dihydrochloride M.p.: >250° C. (from MeOH); $^1$H-NMR in DMSO-$d_6$, δ (ppm): 1.51 (s, 6H), 4.04 (m, 2H), 4.38 (m, 2H), 7.28 (d, J=7 Hz, 1H), 7.67 (t, J=8 Hz, 1H), 7.80 (dd, J=2 Hz and 9 Hz, 1H), 7.92 (d, J=8 Hz, 1H), 8.05–8.12 (m, 2H), 8.25 (s, 1H), 8.69 (d, J=7 Hz, 1H), 8.97 (d, J=9 Hz, 1H), 9.6 (m, 1H), 9.8 (m, 2H), 14.50 (br.s, 1H).

EXAMPLE 49

$N_1$-(7-Chloro-quinolin-4-yl)-$N_2$-(4-cyano-benzyl)-2-methyl-propane-1,2-diamine dihydrochloride M.p.: >250° C. (from EtOH/i-Pr ether; $^1$H-NMR in DMSO-$d_6$, δ (ppm): 1.52 (s, 6H), 4.07 (m, 2H), 4.42 (m, 2H), 7.29 (d, J=7 Hz, 2H), 7.81 (dd, J=2 Hz and 9 Hz), 7.92–8.00 (m, 4H), 8.14 (d, J=2 Hz, 1H), 8.69 (d, J=7 Hz, 1H), 9.01 (d, J=9 Hz, 1H), 9.66 (m, 3H), 14.65 (br.s, 1H).

EXAMPLE 50

$N_1$-(7-Chloro-quinolin-4-yl)-$N_2$-(4-isopropyl-benzyl)-2-methyl-propane-1,2-diamine dihydrochloride M.p.: 210° C. (dec.) (from i-PrOH); $^1$H-NMR in DMSO-$d_6$, δ (ppm): 1.20 (d, J=8.5 Hz, 6H), 1.50 (s, 6H), 2.92 (sept, J=7 Hz, 1H), 4.03 (m, 2H), 4.24 (m, 2H), 7.28 (d, J=7 Hz, 1H), 7.32 (d, J=8 Hz, 2H), 7.62 (d, J=8 Hz, 2H), 7.80 (dd, J=2 Hz and 9 Hz, 1H), 8.13 (d, J=2 Hz, 1H), 8.68 (d, J=7 Hz, 1H), 8.98 (d, J=9 Hz, 1H), 9.60 (m, 3H), 14.60 (br.s, 1H).

EXAMPLE 51

$N_1$-(7-Chloro-quinolin-4-yl)-$N_2$-(bipenyl-4-yl-methyl)-2-methyl-propane-1,2-diamine dihydrochloride M.p.: >250° C. (from MeOH); $^1$H-NMR in DMSO-$d_6$, δ (ppm): 1.54 (s, 6H), 4.06 (m, 2H), 4.34 (m, 2H), 7.28 (d, J=7 Hz, 1H), 7.35–7.55 (m, 3H), 7.65–7.85 (m, 7H), 8.12 (d, J=2 Hz, 1H), 8.69 (d, J=7 Hz, 1H), 8.99 (d, J=9 Hz, 1H), 9.60 (m, 1H), 9.70 (m, 2H), 14.60 (br.s, 1H).

EXAMPLE 52

$N_1$-(7-Chloro-quinolin-4-yl)-$N_2$-(naphthalen-1-yl-methyl)-2-methyl-propane-1,2-diamine dihydrochloride M.p.: 180° C. (dec.) (from MeOH); $^1$H-NMR in DMSO-$d_6$, δ (ppm): 1.46 (s, 6H), 3.60 (s, 2H), 4.43 (s, 2H), 6.77 (d, J=6 Hz, 1H), 7.4–7.6 (m, 4H), 7.75–7.95 (m, 4H), 8.23 (d, J=8 Hz, 1H), 8.42–8.47 (m, 2H).

EXAMPLE 53

$N_1$-(7-Chloro-quinolin-4-yl)-$N_2$-(naphthalen-2-yl-methyl)-2-methyl-propane-1,2-diamine dihydrochloride M.p.: >250° C. (from MeOH/water); $^1$H-NMR in DMSO-$d_6$, δ (ppm): 1.55 (s, 6H), 4.08 (m, 2H), 4.47 (m, 2H), 7.27 (d, J=7 Hz, 1H), 7.55–7.60 (m, 2H), 7.80–8.05 (m, 5H), 8.12 (d, J=2 Hz, 1H), 8.22 (m, 1H), 8.69 (d, J=7 Hz, 1H), 9.00 (d, J=9 Hz, 1H), 9.70 (m, 1H), 9.75 (m, 2H), 14.60 (br.s, 1H).

EXAMPLE 54

$N_1$-(7-Chloro-quinolin-4-yl)-$N_2$-(furan-2-yl-methyl)-2-methyl-propane-1,2-diamine dihydrochloride Yield 36%, m.p.: >250° C. (from EtOH/i-PrOH); $^1$H-NMR in DMSO-$d_6$, δ (ppm): 1.47 (s, 6H), 4.02 (m, 2H), 4.38 (m, 2H), 6.55 (m, 1H), 6.79 (m, 1H), 7.14 (d, J=7.5 Hz, 1H), 7.75–7.85 (m, 2H), 8.21 (d, J=2 Hz, 1H), 8.64 (d, J=7.5 Hz, 1H), 9.07 (d, J=9 Hz, 1H), 9.65 (m, 1H), 9.90 (m, 2H), 14.90 (br.s, 1H).

EXAMPLE 55

$N_1$-(7-Chloro-quinolin-4-yl)-$N_2$-(furan-3-yl-methyl)-2-methyl-propane-1,2-diamine dihydrochloride Yield 74.5%, m.p.: >250° C. (from EtOH/i-PrOH); $^1$H-NMR in DMSO-$d_6$, δ (ppm): 1.48 (s, 6H), 4.02 (m, 2H), 4.19 (m, 2H), 6.95 (m, 1H), 7.27 (d, J=8.5 Hz, 1H), 7.74 (m, 1H), 7.90 (dd, J=2.5 and 9 Hz, 1H), 7.95 (m, 1H), 8.15 (d, J=2.5 Hz, 1H), 8.67 (d, J=8.5 Hz, 1H), 9.03 (d, J=9 Hz, 1H), 9.65 (m, 3H), 14.6 (br.s, 1H).

EXAMPLE 56

$N_1$-(7-Chloro-quinolin-4-yl)-$N_2$-(pyridin-2-yl-methyl)-2-methyl-propane-1,2-diamine trihydrochloride M.p.: >250° C. (from EtOH); $^1$H-NMR in DMSO-$d_6$, δ (ppm): 1.51 (s, 6H), 4.08 (d, J=6 Hz, 2H), 4.55 (m, 2H), 7.28 (d, J=7.5 Hz, 1H), 7.50–7.60 (m, 1H), 7.75–7.87 (m, 2H), 8.0–8.1 (m, 1H), 8.20 (d, J=2 Hz, 1H), 8.60–8.75 (m, 2H), 9.00 (d, J=9 Hz, 1H), 9.70 (m, 1H), 9.90 (m, 2H), 14.90 (br.s, 1H).

EXAMPLE 57

$N_1$-(7-Chloro-quinolin-4-yl)-$N_2$-(pyridin-3-yl-methyl)-2-methyl-propane-1,2-diamine trihydrochloride M.p.: 180° C. (dec.) (from EtOH); $^1$H-NMR in DMSO-$d_6$, δ (ppm): 1.54 (s, 6H), 4.07 (s, 2H), 4.38 (s, 2H), 7.30 (d, J=7.5 Hz, 1H), 7.49 (dd, J=6 Hz and 8.5 Hz, 1H), 7.78 (dd, J=2 Hz and 9 Hz, 1H), 8.16 (d, J=2 Hz, 1H), 8.23–8.28 (m, 1H), 8.60 (dd, J=2 Hz and 6 Hz, 1H), 8.67 (d, J=7.5 Hz, 1H), 8.90 (d, J=2 Hz, 1H), 9.08 (d, J=9 Hz, 1H), 9.70 (m, 1H), 10.0 (m, 2H), 14.8 (br., 1H).

EXAMPLE 58

$N_1$-(7-Chloro-quinolin-4-yl)-$N_2$-(quinolin-4-yl-methyl)-2-methyl-propane-1,2-diamine trihydrochloride M.p.: 207–209° C. (from MeOH); $^1$H-NMR in DMSO-$d_6$, δ (ppm): 1.66 (s, 6H), 4.25 (d, J=6.5 Hz, 2H), 5.09 (m, 2H), 7.36 (d, J=7 Hz, 1H), 7.76 (dd, J=2 Hz and 9 Hz, 1H), 7.93 (m,1H), 8.10 (m, 1H), 8.23 (d, J=2 Hz, 1H), 8.44 (m, 2H), 8.66 (m, 2H), 9.10 (d, J=9 Hz, 1H), 9.34 (d, J=7 Hz, 1H), 9.85 (m, 1H), 10.66 (m, 2H), 15.00 (br.s, 1H).

EXAMPLE 59

$N_1$-(7-Chloro-quinolin-4-yl)-$N_2$-(2,4-bis-trifluoromethyl-benzyl)-2-methyl-propane-1,2-diamine dihydrochloride M.p.: 260° C. (dec.) (from MeOH); $^1$H-NMR in DMSO-$d_6$, δ (ppm): 1.54 (s, 6H), 4.12 (s, 2H), 4.50 (s, 2H), 7.30 (d, J=7.5 Hz, 1H), 7.78 (dd, J=2 Hz and 9 Hz, 1H), 8.11 (s, 1H), 8.20 (d, J=2 Hz, 1H), 8.23–8.28 (m, 1H), 8.60–8.70 (m, 2H), 9.08 (d, J=9 Hz, 1H), 9.75 (m, 1H), 10.35 (m, 2H), 14.80 (br.s, 1H).

EXAMPLE 60

(1S,2S)-$N_1$-(7-Chloro-quinolin-4-yl)-$N_2$-(benzyl)-cyclohexane-1,2-diamine hydrochloride (1:2)

0.39 g of N-(7-chloro-quinolin-4-yl)-cyclohexane-1,2-diamine and 0.13 ml of benzaldehyde were stirred at 20° C. in 3 ml of ethanol for 3 hrs. The solvent was evaporated in order to complete the reaction. The resulting Schiff's base was again dissolved in 3 ml of ethanol, cooled in ice under argon and then treated portionwise with 0.3 g of sodium borohydride and stirred without cooling for a further 20 hrs. Excess reducing agent was decomposed by the addition of 3 ml of acetone. Thereafter, the mixture was diluted with 30 ml of 0.3N NaOH and extracted twice with 30 ml of dichloromethane each time. The crude product obtained from these extracts was purified by flash chromatography on silica gel with ethyl acetate and ethyl acetate/methanol 5:1. The purified product was converted into the hydrochloride with ethanolic hydrochloric acid and precipitated by dilution with 2-butanone. Yield: 260 mg (54%), m.p. >200° C. (dec.).

ISP mass spectrum: peaks inter alia at 366 (M+H$^+$); $^1$H-NMR in DMSO-$d_6$, δ (ppm): 1.25–2.40 (m, 8H), 3.75 (m, 1H), 4.30 (m, 3H), 7.18 (d, J=7, 2H), 7.37 (m, 3H), 7.54 (m, 2H), 7.78 (dd, J=2 Hz and 9 Hz, 1H), 8.10 (d, 1H, J=2 Hz, 1H), 8.62 (d, J=7 Hz, 1H), 8.88 (d, J=9 Hz, 1H), 9.40 (m, 1H).

The following compounds were obtained in an analogous manner using the correspondingly substituted benzaldehydes:

EXAMPLES 61

(1S,2S)-$N_1$-(7-Chloro-quinolin-4-yl)-$N_2$-(4-chloro-benzyl)-cyclohexane-1,2-diamine dihydrochloride M.p. 210° C. (from EtOH/2-butanone); EI mass spectrum: fragments at 399 (M+), 274; $^1$H-NMR in DMSO-$d_6$, δ (ppm): 1.25–2.40 (m, 8H), 3.75 (m, 1H), 4.30 (m, 3H), 7.12 (d, J=7, 2H), 7.43 (d, J=8.4, 2H), 7.59 (d, J=8.4, 2H), 7.76 (dd, J=2 Hz and 9 Hz, 1H), 8.09 (d, J=2 Hz, 1H), 8.59 (d, J=7 Hz, 1H,), 8.87 (d, J=9 Hz, 1H), 9.32 (m, 1H).

EXAMPLE 62

(1S,2S)-$N_1$-(7-Chloro-quinolin-4-yl)-$N_2$-(2,4-dichloro-benzyl)-cyclohexane-1,2-diamine dihydrochloride M.p. 204–220° C. (from EtOH/2-butanone); ISP mass spectrum: peaks at 434 (M+H+); $^1$H-NMR in DMSO-$d_6$, δ (ppm): 1.25–2.40 (m, 8H), 3.83 (m, 1H), 4.27 (s, 2H), 4.40 (m,1H), 7.12 (d, J=7 Hz, 2H), 7.43 (dd, J=2.1 Hz and 8.3 Hz, 1H), 7.60 (d, J=2.1 Hz, 1H), 7.75 (dd, J=2 Hz and 9 Hz, 1H), 7.80 (d, J=8.3 Hz, 1H), 8.14 (d, J=2 Hz, 1H), 8.60 (d, J=7 Hz, 1H), 8.93 (d, J=9 Hz, 1H), 9.50 (m, 1H).

EXAMPLE 63

(1S,2S)-$N_1$-(7-Chloro-quinolin-4-yl)-$N_2$-(3,4-dichloro-benzyl)-cyclohexane-1,2-diamine dihydrochloride M.p.: dec. from 210° C. (from EtOH/2-butanone); EI mass spectrum: fragments at 433 (M+, 8%), 274 (100%), 179 (45%), 159 (38%); ISP mass spectrum: peaks at 434 (M+H+); $^1$H-NMR in DMSO-$d_6$, δ (ppm): 1.25–2.40 (m, 8H), 3.75 (m, 2H), 4.30 (m, 2H), 7.14 (d, J=7 Hz, 2H), 7.58 (m, 1H), 7.64 (m, 1H), 7.78 (dd, J=2 Hz and 9 Hz, 1H), 7.93 (d, J=2 Hz, 1H), 8.12 (d, J=2 Hz, 1H), 8.60 (d, J=7 Hz, 1H), 8.92 (d, J=9 Hz, 1H), 9.30 (m, 2H), 9.50 (d, J=8 Hz, 1H), 10.25 (m, 1H), 14.55 (br.s, 1H).

EXAMPLE 64

(1S,2S)-$N_1$-(7-Chloro-quinolin-4-yl)-$N_2$-(2,4-bis-trifluoromethyl-benzyl)-cyclohexane-1,2-diamine dihydrochloride M.p. from 185° C. (from EtOH/2-butanone); dec.; ISP mass spectrum: peaks at 502 (M+H+); $^1$H-NMR in DMSO-$d_6$, δ (ppm): 1.25–2.40 (m, 8H), 3.2–3.7 (m, 2H), 4.27 (m, 3H), 4.40 (m, 1H), 7.12 (d, J=7 Hz, 2H), 7.73 (dd, J=2 Hz and 9 Hz, 1H), 7.93 (m, 2H), 8.10 (m, 2H), 8.57 (d, J=7 Hz, 1H), 8.82 (d, J=9, 1H), 9.36 (m, 1H).

EXAMPLE 65

(1S,2S)-$N_1$-(7-Chloro-quinolin-4-yl)-$N_2$-(3,4,5-trimethoxy-benzyl)-cyclohexane-1,2-diamine dihydrochloride M.p. >250° C. (from EtOH/2-butanone); ISP mass spectrum: peaks at 456 (M+H+); $^1$H-NMR in DMSO-$d_6$, δ (ppm): 1.25–2.40 (m, 8H), 3.60 (s, 3H), 3.70 (s, 6H), 3.75–4.50 (m, 4H), 6.97 (s, 2H), 7.14 (d, J=7 Hz, 2H), 7.74 (dd, J=2 Hz and 9 Hz, 1H), 8.14 (d, J=2 Hz, 1H), 8.61 (d, J=7 Hz, 1H), 8.94 (d, J=9 Hz, 1H), 9.48 (m, 1H)

EXAMPLE 66

(1S,2S)-$N_1$-(7-Chloro-quinolin-4-yl)-$N_2$-(4-dimethylamino-benzyl)-cyclohexane-1,2-diamine dihydrochloride M.p. 220–223° C. (from EtOH/Et$_2$O); ISP mass spectrum: peaks at 409 (M+H+, 50%), 276 (70%), 134 (100%); $^1$H-NMR in DMSO-$d_6$, δ (ppm): 1.25–2.40 (m, 8H), 2.90 (s, 6H), 3.60 (m, 2H), 4.18 (m, 2H), 4.32 (m, 1H), 6.85 (m, 2H), 7.14 (d, J=7 Hz, 2H), 7,38 (d, J=8 Hz, 2H), 7.78 (dd, J=2 Hz and 9 Hz, 1H) 8.12 (d, J=2 Hz, 1H), 8.61 (m, 1H), 8.91 (d, J=9 Hz, 1H), 9.05 (m, 1H), 9.45 (d, J=8 Hz, 1H), 9.75 (m, 1H), 14.55 (br.s, 1H).

EXAMPLE 67

(1S,2S)-$N_1$-(7-Chloro-quinolin-4-yl)-$N_2$-(4-cyano-benzyl)-cyclohexane-1,2-diamine dihydrochloride M.p. 226–230° C. (from EtOH/Et$_2$O); ISP mass spectrum: peaks at 391 (M+H+, 100%), 276 (33%); $^1$H-NMR in DMSO-$d_6$, δ (ppm): 1.25–2.40 (m, 8H), 3.71 (m, 1H), 4.25–4.40 (m, 3H), 7.16 (d, J=7 Hz, 2H), 7.77–7.81 (m, 3H), 7.88 (d, J=8 Hz, 2H), 8.08 (d, J=2 Hz, 1H), 8.62 (d, J=7 Hz, 1H), 8.86 (d, J=9 Hz, 1H), 9.41 (d, J=8 Hz, 1H), 9.50 (m, 1H), 10.5 (m 1H), 14.40 (br.s, 1H).

EXAMPLE 68 cis-$N_1$-(7-Chloro-quinolin-4-yl)-$N_3$-(4-chloro-benzyl)-cyclopentane-1,3-diamine dihydrochloride 0.24 g of cis-N-(7-chloro-quinolin-4-yl)-cyclopentyl-1,3-diamine and 0.21 g of 4-chloro-benzaldehyde were boiled under reflux in 50 ml of ethanol overnight. After evaporation of the solvent the residue was again taken up in 50 ml of ethanol, 0.1 g of sodium borohyride was added thereto and the mixture was left to react at room temperature for 6 hrs. The excess sodium borohydride was then decomposed by the dropwise addition of 5 ml of glacial acetic acid and the solvent was evaporated. After the addition of 10 ml of methanol the mixture was again evaporated. Addition of methanol and evaporation were repeated once more. The residue was thereafter purified by chromatography on 30 g of silica gel with a mixture of dichloromethane and methanol (in the ratio by volume 10:1). The product-containing fractions were combined and evaporated, and the residue was taken up in 5 ml of ethanol. After the addition of 5 ml of 3N isopropanolic hydrochloric acid the hydrochloride of the product separated and was recrystallized from ethanol/diethyl ether.

Yield: 0.55 g (78%) of colourless crystalline cis-$N_1$-(7-chloro-quinolin-4-yl)-$N_3$-(4-chloro-benzyl)-cyclopentane-1,4-diamine dihydrochloride; m.p 191–193° C. (from EtOH/Et$_2$O); EI mass spectrum with peaks at 385 (M+, 38%), 246 (92%), 205 (98%), 178 (44%), 125 (100%); $^1$H-NMR in DMSO-$d_6$, δ (ppm): 2.00–2.30 (m, 5H), 2.55–2.65 (m, 1H), 3.34 (m, 2H), 3.58 (m, 1H), 4.20 (s, 2H), 4.36 (m, 1H), 6.91 (d, J=7 Hz, 1H), 7.53 (d, J=8 Hz, 2H), 7.66 (d, J=8 Hz, 2H), 7.75 (dd, J=2 and 9 Hz, 1H), 8.06 (d, J=2 Hz, 1H), 8.60 (d, J=7 Hz, 1H), 9.06 (d, J=9 Hz, 1H), 9.50 (m, 1H), 9.90 (m, 1H), 14.30 (br.s, 1H).

EXAMPLE 69 cis-$N_1$-(7-Chloro-quinolin-4-yl)-$N_4$-(4-dimethylamino-benzyl)-cyclohexane-1,4-diamine trihydrochloride 1 g of cis-N-(7-chloro-quinolin-4-yl)-cyclohexyl-1,4-diamine and 0.54 g of 4-dimethylamino-benzaldehyde were boiled on a water separator in 50 ml of toluene overnight. After evaporation of the toluene the residue was taken up in 20 ml of ethanol and 5 ml of dichloromethane, 0.13 g of sodium borohydride was added thereto and the mixture was left to react at room temperature for 6 hours. The excess sodium borohydride was decomposed with 2.5 ml of glacial acetic acid and the solvent was evaporated. After the addition of 10 ml of methanol the mixture was again evaporated. Addition of methanol and evaporation were repeated once. The residue was thereafter purified by chromatography on 50 g of silica gel with a mixture of dichloromethane, methanol and water (in the ratio by volume 8:3:0.6). The product-containing fractions were combined and evaporated, and the residue was taken up in 5 ml of ethanol. After the addition of 5 ml of 3N isopropanolic hydrochloric acid the hydrochloride of the product separated and was recrystallized from ethanol/diethyl ether.

Yield: 1.5 g (80%) of colourless crystalline trihydrochloride; m.p. 228° C. ISP mass spectrum: peaks at 409 (M+H$^+$, 100%), 276 (75%), 134 (76%); $^1$H-NMR in DMSO-d$_6$, δ (ppm): 1.70–2.20 (m, 8H), 2.97 (s, 3H), 3.17 (m, 1H), 4.09 (m, 3H), 6.92 (d, J=7 Hz, 1H), 7.05 (m, 2H), 7.57 (m, 2H), 7.78 (dd, J=2 and 9 Hz, 1H), 8.14 (d, J=2 Hz, 1H), 8.59 (d, J=7 Hz, 1H), 8.71 (m, 1H), 8.90 (d, J=9 Hz, 1H), 9.35 (m, 2H), 14.65 (br.s, 1H).

The following compounds were obtained in an analogous manner using the correspondingly substituted benzaldehydes:

EXAMPLE 70 cis-N$_1$-(7-Chloro-quinolin-4-yl)-N$_4$-(benzyl)-cyclohexane-1,4-diamine dihydrochloride Yield 68%; m.p. >250° C. (from EtOH/Et$_2$O); ISP mass spectrum: peaks at 366 (M+H$^+$, 100%), 276 (85%); $^1$H-NMR in DMSO-d$_6$, δ (ppm): 1.68–1.84 (m, 2H), 1.90–2.30 (m, 6H), 3.20 (m, 1H), 4.08 (m, 1H), 4.18 (m, 2H), 6.93 (d, J=7 Hz, 1H), 7.40–7.50 (m, 3H), 7.60–7.70 (m, 2H), 7.80 (dd, J=2 Hz and 9 Hz, 1H), 8.12 (d, J=2 Hz, 1H), 8.59 (d, J=7 Hz, 1H), 8.69 (m, 1H), 8.89 (d, J=9 Hz, 1H), 9.44 (m, 2H), 9.32 (m, 1H), 14.53 (s, 1H).

EXAMPLE 71 cis-N$_1$-(7-Chloro-quinolin-4-yl)-N$_4$-(3-chloro-benzyl)-cyclohexane-1,4-diamine dihydrochloride Yield 70%; m.p. 198–200° C. (from EtOH/Et$_2$O); ISP mass spectrum: peaks at 400 (M+H$^+$, 100%), 276 (62%); $^1$H-NMR in DMSO-d$_6$, δ (ppm): 1.70–2.24 (m, 8H), 3.25 (m, 1H), 4.08 (m, 1H), 4.21 (m, 2H), 6.92 (d, J=7 Hz, 1H), 7.45–7.53 (m, 2H), 7.61–7.67 (m, 1H), 7.78 (dd, J=2 and 9 Hz, 1H), 7.80 (m, 1H), 8.13 (d, J=2 Hz, 1H), 8.59 (d, J=7 Hz, 1H), 8.70 (m, 1H), 8.89 (d, J=9 Hz, 1H), 9.56 (m, 2H), 14.60 (br.s, 1H).

EXAMPLE 72 cis-N$_1$-(7-Chloro-quinolin-4-yl)-N$_4$-(4-chloro-benzyl)-cyclohexane-1,4-diamine dihydrochloride Yield 39%; m.p. 190–195° C. (from EtOH/Et$_2$O); ISP mass spectrum: peaks at 400 (M+H$^+$, 100%), 276 (90%), 125 (100%); $^1$H-NMR in DMSO-d$_6$, δ (ppm): 1.70–2.23 (m, 8H), 3.16 (m, 1H), 4.08 (m, 1H), 4.18 (m, 2H), 6.90 (d, J=7 Hz, 1H), 7.51 (d, J=8 Hz, 2H), 7.71 (d, J=8 Hz, 2H), 7.77 (dd, J=2 Hz and 9 Hz, 1H), 8.18 (d, J=2 Hz, 1H), 8.58 (d, J=7 Hz, 1H), 8.73 (m, 1H), 8.92 (d, J=9 Hz, 1H), 9.65 (m, 2H), 14.83 (s, 1H).

EXAMPLE 73 cis-N$_1$-(7-Chloro-quinolin-4-yl)-N$_4$-(2,4-dichloro-benzyl)-cyclohexane-1,4-diamine dihydrochloride Yield 55%; m.p. 204–205° C. (from EtOH/Et$_2$O); ISP mass spectrum: peaks at 434 (M+H$^+$, 100%), 159 (25%); $^1$H-NMR in DMSO-d$_6$, δ (ppm): 1.74–2.25 (m, 8H), 3.34 (m, 1H), 4.10 (m, 1H), 4.30 (m, 2H), 6.95 (d, J=7 Hz, 1H), 7.57 (dd, J=2 and 8 Hz, 1H), 7.76 (d, J=2 Hz, 1H), 7.79 (dd, J=2 and 9 Hz, 1H), 7.92 (d, J=8 Hz, 1H), 8.12 (d, J=2 Hz, 1H), 8.59 (d, J=7 Hz, 1H), 8.70 (m, 1H), 8.88 (d, J=9 Hz, 1H), 9.55 (m, 2H), 14.53 (br.s, 1H).

EXAMPLE 74 cis-N$_1$-(7-Chloro-quinolin-4-yl)-N$_4$-(3,4-dichloro-benzyl)-cyclohexane-1,4-diamine dihydrochloride Yield 35%; m.p. 212° C. (from EtOH/Et$_2$O); ISP mass spectrum: peaks at 434 (M+H$^+$, 100%), 276 (68%), 159 (86%); $^1$H-NMR in DMSO-d$_6$, δ (ppm): 1.72–2.25 (m, 8H), 3.24 (m, 1H), 4.07 (m, 1H), 4.21 (m, 2H), 6.92 (d, J=7 Hz, 1H), 7.67 (dd, J=1.5 and 8 Hz, 1H), 7.73 (d, J=Hz, 1H), 7.79 (dd, J=2 and 9 Hz, 1H), 8.02 (d, J=1.5 Hz, 1H), 8.12 (d, J=2 Hz, 1H), 8.59 (d, J=7 Hz, 1H), 8.72 (m, 1H), 8.89 (d, J=9 Hz, 1H), 9.60 (m, 2H), 14.57 (br.s, 1H).

EXAMPLE 75 cis-N$_1$-(7-Chloro-quinolin-4-yl)-N$_4$-(3,5-dichloro-benzyl)-cyclohexane-1,4-diamine dihydrochloride Yield 16%; m.p. 204–205° C. (from EtOH/Et$_2$O); ISP mass spectrum: peaks at 434 (M+H$^+$, 100%); $^1$H-NMR in DMSO-d$_6$, δ (ppm): 1.72–2.23 (m, 8H), 3.26 (m, 1H), 4.08 (m, 1H), 4.22 (m, 2H), 6.93 (d, J=7 Hz, 1H), 7.69 (m, 1H), 7.77–7.83 (m, 3H), 8.10 (d, J=2 Hz, 1H), 8.60 (d, J=7 Hz, 1H), 8.70 (m, 1H), 8.88 (d, J=9 Hz, 1H), 9.55 (m, 2H), 14.47 (br.s, 1H).

EXAMPLE 76 cis-N$_1$-(7-Chloro-quinolin-4-yl)-N$_4$-(4-chloro-3-fluoro-benzyl)-cyclohexane-1,4-diamine dihydrochloride Yield 70%; m.p. 158° C. (from EtOH/i-PrOH); ISP mass spectrum: peaks at 418 (M+H$^+$, 100%), 276 (88%), 143 (61%); $^1$H-NMR in DMSO-d$_6$, δ (ppm): 1.70–1.85 (m, 2H), 1.90–2.20 (m, 6H), 3.11 (m, 1H), 4.06 (m, 1H), 4.22 (m, 2H), 6.92 (d, J=7 Hz, 1H), 7.53 (m, 1H), 7.69 (t, J=8 Hz, 1H), 7.76–7.86 (m, 2H), 8.11 (d, J=2 Hz, 1H), 8.59 (d, J=7 Hz, 1H), 8.68 (m, 1H), 8.87 (d, J=9 Hz, 1H), 9.60 (m, 2H), 14.50 (br.s, 1H).

EXAMPLE 77 cis-N$_1$-(7-Chloro-quinolin-4-yl)-N$_4$-(3,5-bis-trifluoromethyl-benzyl)-cyclohexane-1,4-diamine dihydrochloride Yield 41%; m.p. 215° C. (from EtOH/Et$_2$O); ISP mass spectrum: peaks at 502 (M+H$^+$, 67%), 276 (100%); $^1$H-NMR in DMSO-d$_6$, δ (ppm): 1.75–2.25 (m, 8H), 3.36 (m, 1H), 4.09 (m, 1H), 4.43 (m, 2H), 6.94 (d, J=7 Hz, 1H), 7.80 (dd, J=2 and 9 Hz, 1H), 8.13 (d, J=2 Hz, 1H), 8.19 (m, 1H), 8.48 (m, 2H), 8.60 (d, J=7 Hz, 1H), 8.76 (m, 1H), 8.89 (d, J=9 Hz, 1H), 9.70 (m, 2H), 14.60 (br.s, 1H).

EXAMPLE 78 cis-N$_1$-(7-Chloro-quinolin-4-yl)-N$_4$-(2-hydroxy-benzyl)-cyclohexane-1,4-diamine dihydrochloride Yield 92%; m.p. 200–202° C. (from EtOH/Et$_2$O); ISP mass spectrum: peaks at 382 (M+H$^+$, 100%); $^1$H-NMR in DMSO-$d_6$, δ (ppm): 1.72–2.24 (m, 8H), 3.21 (m, 1H), 4.11 (m, 3H), 6.85 (t, J=8 Hz, 1H), 6.95 (d, J=7 Hz, 1H), 7.00 (d, J=8 Hz, 1H), 7.24 (dt, J=2 and 8 Hz, 1H), 7.49 (dd, J=2 and 8 Hz, 1H), 7.80 (dd, J=2 and 9 Hz, 1H), 8.13 (d, J=2 Hz, 1H), 8.59 (d, J=7 Hz, 1H), 8.69 (m, 1H), 8.88 (d, J=9 Hz, 1H), 9.00 (m, 2H), 10.27 (s, 1H ), 14.55 (br.s, 1H).

EXAMPLE 79 cis-$N_1$-(7-Chloro-quinolin-4-yl)-$N_4$-(2-hydroxy-4-methoxy-benzyl)-cyclohexane-1,4-diamine dihydrochloride Yield 75%; m.p. 200° C. (from EtOH/$Et_2O$); ISP mass spectrum: peaks at 412 (M+$H^+$, 100%); $^1$H-NMR in DMSO-$d_6$, δ (ppm): 1.70–2.22 (m, 8H), 3.14 (m, 1H), 3.71 (s, 3H), 4.04 (m, 3H), 6.46 (dd, J=2 and 8 Hz, 1H), 6.54 (d, J=2 Hz, 1H), 6.94 (d, J=7 Hz, 1H), 7.37 (d, J=8 Hz, 1H), 7.80 (dd, J=2 Hz and 9 Hz, 1H), 8.13 (d, J=2 Hz, 1H), 8.60 (d, J=7 Hz, 1H), 8.70 (m, 1H), 8.86 (d, J=9 Hz, 1H), 8.88 (m, 1H), 10.30 (s, 1H), 14.53 (br.s, 1H).

EXAMPLE 80 cis-$N_1$-(7-Chloro-quinolin-4-yl)-$N_4$-(2-hydroxy-5-methoxy-benzyl)-cyclohexane-1,4-diamine dihydrochloride Yield 86%; m.p. 180–185° C. (from EtOH/$Et_2O$); ISP mass spectrum: peaks at 412 (M+$H^+$, 4%), 269 (49%), 187 (83%), 165 (100%); $^1$H-NMR in DMSO-$d_6$, δ (ppm): 1.70–2.25 (m, 8H), 3.21 (m, 1H), 3.70 (s, 3H), 4.09 (m, 3H), 6.80–6.92 (m, 3H), 7.16 (d, J=2 Hz, 1H), 7.80 (dd, J=2 Hz and 9 Hz, 1H), 8.09 (d, J=2 Hz, 1H), 8.59 (d, J=7 Hz, 1H), 8.61 (s, 1H), 8.85 (d, J=9 Hz, 1H), 9.02 (m, 2H), 9.75 (m, 1H), 14.45 (br.s, 1H).

EXAMPLE 81 cis-$N_1$-(7-Chloro-quinolin-4-yl)-$N_4$-(2,4-dimethoxy-benzyl)-cyclohexane-1,4-diamine dihydrochloride Yield 87%; m.p. >250° C. (from EtOH/$Et_2O$); ISP mass spectrum: peaks at 426 (M+$H^+$, 100%), 276 (54%), 187 (55%), 165 (60%), 151 (49%); $^1$H-NMR in DMSO-$d_6$, δ (ppm): 1.70–2.20 (m, 8H), 3.08 (m, 1H), 3.79 (s, 3H), 3.83 (s, 3H), 4.05 (m, 3H), 6.59 (dd, J=2 and 8 Hz, 1H), 6.64 (d, J=2 Hz, 1H), 6.92 (d, J=7 Hz, 1H), 7.44 (d, J=8 Hz, 2H), 7.80 (dd, J=2 Hz and 9 Hz, 1H), 8.12 (d, J=2 Hz, 1H), 8.59 (d, J=7 Hz, 1H), 8.73 (m, 1H), 8.88 (d, J=9 Hz, 1H), 8.92 (m, 2H), 14.52 (s, 1H).

EXAMPLE 82 cis-$N_1$-(7-Chloro-quinolin-4-yl)-$N_4$-(3,5-dimethoxy-benzyl)-cyclohexane-1,4-diamine dihydrochloride Yield 67%; m.p. 197–198° C. (from EtOH/i-PrOH); ISP mass spectrum: peaks at 426 (M+$H^+$, 100%), 276 (90%), 151 (93%); $^1$H-NMR in DMSO-$d_6$, δ (ppm): 1.70–2.23 (m, 8H), 3.20 (m, 1H), 4.11 (m, 3H), 6.53 (t, J=2 Hz, 1H), 6.69 (d, J=2 Hz, 2H), 6.93 (d, J=7 Hz, 1H), 7.80 (dd, J=2 and 9 Hz, 1H), 8.11 (d, J=2 Hz, 1H), 8.59 (d, J=7 Hz, 1H), 8.71 (m, 1H), 8.89 (d, J=9 Hz, 1H), 9.44 (m, 2H), 14.50 (br.s, 1H).

EXAMPLE 83 cis-$N_1$-(7-Chloro-quinolin-4-yl)-$N_4$-(4-methylsulphanyl-benzyl)-cyclohexane-1,4-diamine dihydrochloride Yield 83%; m.p. 181–182° C. dec. (from EtOH/$Et_2O$); ISP mass spectrum: peaks at 412 (M+$H^+$, 100%), 276 (26%); $^1$H-NMR in DMSO-$d_6$, δ (ppm): 1.68–1.85 (m, 2H), 1.90–2.25 (m, 6H), 3.19 (m, 1H), 3.34 (s, 3H), 4.08 (m, 1H), 4.14 (m, 2H), 6.92 (d, J=7 Hz, 1H), 7.31 (d, J=8 Hz, 2H), 7.57 (d, H=8 Hz, 2H), 7.79 (dd, J=2 Hz and 9 Hz, 1H), 8.10 (d, J=2 Hz, 1H), 8.59 (d, J=7 Hz, 1H), 8.64 (m, 1H), 8.87 (d, J=9 Hz, 1H), 9.38 (m, 2H), 14.50 (br.s, 1H).

EXAMPLE 84 cis-$N_1$-(7-Chloro-quinolin-4-yl)-$N_4$-(4-nitro-benzyl)-cyclohexane-1,4-diamine dihydrochloride Yield 52%; m.p. >260° C. (from EtOH/$Et_2O$); ISP mass spectrum: peaks at 411 (M+$H^+$, 100%), 276 (25%); $^1$H-NMR in DMSO-$d_6$, δ (ppm): 1.70–2.24 (m, 8H), 3.25 (m, 1H), 4.09 (m, 1H), 4.34 (m, 2H), 6.92 (d, J=7 Hz, 1H), 7.80 (dd, J=2 Hz and 9 Hz, 1H), 7.94 (d, J=8 Hz, 2H), 8.10 (d, J=2 Hz, 1H), 8.31 (d, J=8 Hz, 2H), 8.59 (d, J=7 Hz, 1H), 8.70 (m, 1H), 8.88 (d, J=9 Hz, 1H), 9.64 (m, 2H), 14.45 (br.s, 1H).

EXAMPLE 85 cis-$N_1$-(7-Chloro-quinolin-4-yl)-$N_4$-(4-diethylamino-benzyl)-cyclohexane-1,4-diamine trihydrochloride Yield 52%; m.p. >260° C. (from EtOH/$Et_2O$); ISP mass spectrum: peaks at 411 (M+$H^+$, 100%), 276 (25%); $^1$H-NMR in DMSO-$d_6$, δ (ppm): 1.70–2.24 (m, 8H), 3.25 (m, 1H), 4.09 (m, 1H), 4.34 (m, 2H), 6.92 (d, J=7 Hz, 1H), 7.80 (dd, J=2 Hz and 9 Hz, 1H), 7.94 (d, J=8 Hz, 2H), 8.10 (d, J=2 Hz, 1H), 8.31 (d, J=8 Hz, 2H), 8.59 (d, J=7 Hz, 1H), 8.70 (m, 1H), 8.88 (d, J=9 Hz, 1H), 9.64 (m, 2H), 14.45 (br.s, 1H).

EXAMPLE 86 cis-$N_1$-(7-Chloro-quinolin-4-yl)-$N_4$-(4-cyano-benzyl)-cyclohexane-1,4-diamine dihydrochloride Yield 60%; m.p. >250° C. (from EtOH/i-PrOH); ISP mass spectrum: peaks at 391 (M+$H^+$, 100%); $^1$H-NMR in DMSO-$d_6$, δ (ppm): 1.71–1.87 (m, 2H), 1.92–2.25 (m, 8H), 3.22 (m, 1H), 4.08 (m, 1H), 4.29 (m, 2H), 6.93 (d, J=7 Hz, 1H), 7.79 (dd, J=2 Hz and 9 Hz, 1H), 7.89 (d, J=8 Hz, 2H), 7.94 (d, J=8 Hz, 2H), 8.13 (d, J=2 Hz, 1H), 8.59 (d, J=7 Hz, 1H), 8.70 (m, 1H), 8.89 (d, J=9 Hz, 1H), 9.71 (m, 2H), 14.56 (br.s, 1H).

EXAMPLE 87 cis-$N_1$-(7-Chloro-quinolin-4-yl)-$N_4$-(biphenyl-4-yl-methyl)-cyclohexane-1,4-diamine dihydrochloride Yield 86%; m.p. 210–212° C. (from EtOH/$Et_2O$); ISP mass spectrum: peaks at 442 (M+$H^+$, 100%), 167 (55%); $^1$H-NMR in DMSO-$d_6$, δ (ppm): 1.70–1.86 (m, 2H), 1.93–2.30 (m, 6H), 3.25 (m, 1H), 4.08 (m, 1H), 4.23 (m, 2H), 6.93 (d, J=7 Hz, 1H), 7.40 (m, 1H), 7.49 (m, 2H), 7.60–7.83 (m, 7H), 8.13 (d, J=2 Hz, 1H), 8.60 (d, J=7 Hz, 1H), 8.71 (m, 1H), 8.91 (d, J=9 Hz, 1H), 9.50 (m, 2H), 14.56 (br.s, 1H).

EXAMPLE 88 trans-$N_1$-(7-Chloro-quinolin-4-yl)-$N_4$-[2-(3,4-dimethoxy-phenyl)-ethyl]-cyclohexane-1,4-diamine dihydrochloride 275 mg 4-(7-chloroquinolin-4-ylamino)-cyclohexanone (see Example 124) and 181 mg of homoveratrylamine were boiled at reflux for 3 hours in 5 ml of ethanol in the presence of molecular sieve. The solution, which was cooled and freed from the molecular sieve, was concentrated to dryness. The residue was again taken up in 5 ml of ethanol and treated under argon at +5° C. with 37 mg of sodium borohydride. After 1 hour the mixture was concentrated and the residue was suspended in dichloromethane. The excess reducing agent was decomposed by the addition of 2 ml of 3N sodium hydroxide solution. The mixture was diluted with water and the dichloromethane was separated. The dried organic phase was concentrated. The residue was chromatographed on silica gel with dichloromethane/methanol (3:1). The free base obtained was crystallized as the dihydrochloride by treatment with 3N hydrochloric acid in methanol. Yield: 280 mg (54%) of white crystals, m.p. 210° C.

ISP mass spectrum: peaks at 440.5 ((M+H)$^+$, 23%), 276.4 (75%), 221 (100 $^1$H NMR of the free base in CDCl$_3$ d (ppm): 1.32 (br, 5H), 2.06 (br, 2H), 2.23 (br, 2H), 2.55 (br, 1H), 2.77 (m, 2H), 2.91 (m, 2H), 3.87 (s, 1H), 3,88 (s, 1H), 4.80 (d, 1H), 6.42 (d, J=6 Hz, 1H), 6.78 (m, 3H), 7.35 (dd, J=2 and 9 Hz, 1H), 7.61 (d, J=9 Hz, 1H), 7.94 (d, J=2 Hz, 1H), 8.52 (d, J=6 Hz).

EXAMPLE 89 trans-N$_1$-(7-Chloro-quinolin-4-yl)-N$_4$-phenethyl-cyclohexane-1,4-diamine dihydrochloride Analogously to Example 88 using phenethylamine. Yield: 23% of white crystals (from ethanol/ether). Dec. from 210° C.

ISP mass spectrum: peaks at 380 ((M+H)$^+$, 35%), 276 (100%); $^1$H NMR in DMSO-d$_6$, δ (ppm): 1.65 (m, 4H), 2.05 (br, 2H), 2.25 (br, 2H), 3.09 (br, 5H), 3.90 (br, 1H), 7.05 (d, J=7 Hz, 1H), 7.31 (m, 5H), 7.75 (dd, J=2 and 7.5 Hz, 1H), 8.13 (d, J=2Hz, 1H), 8.53 (d, J=7 Hz, 1H), 8.84 (d, J=7.5 Hz, 1H), 9.15 (d, J=9 Hz, 1H), 9.46 (br, 2H), 14.6 (br, 1H).

EXAMPLE 90 trans-N$_1$-(7-Chloro-quinolin-4-yl)-N$_4$-(3,5-dimethoxy-phenyl)-cyclohexane-1,4-diamine hydrochloride Analogously to Example 88 using 3,5-dimethoxyaniline and 72 hours reflux for imine formation. Yield: 8%, Dec. 204° C.

EI mass spectrum: peaks at 411 (M$^+$, 100%), 258 (35%), 192 (30%); $^1$H NMR of the free base in CDCl$_3$ δ (ppm): 1.66 (br, 4H), 2.05 (br, 4H), 3.40 (br, 1H), 3.70 (br, 1H), 3.75 (s, 6H), 3.85 (br, 1H), 6.52 (br, 3H), 7.04 (d, J=7.5 Hz, 1H), 7.76 (dd, J=2 and 9 Hz, 1H), 8.10 (d, J=2 Hz, 1H), 8.51 (br, 1H), 8.81 (d, J=9 Hz, 1H), 9.09 (d, J=7.5 Hz, 1H), 14.4 (br, 1H).

EXAMPLE 91 trans-N$_1$-(7-Chloro-quinolin-4-yl)-N$_4$-[2-(2,4-dichloro-phenyl)-ethyl]-cyclohexane-1,4-diamine dihydrochloride Analogously to Example 88 using 2,4-dichlorophenethylamine. Yield: 35% of white crystals (from methanol/ether), dec. 230° C.

ISP mass spectrum: peaks at 448 ((M+H)$^+$, 100%); $^1$H NMR of the free base in CDCl$_3$ δ (ppm): 1.25 (br, 4H), 1.75 (br, 1H), 2.15 (br, 2H), 2.24 (br, 2H), 2.60 (br, 1H), 2.92 (m, 5H), 3.55 (br, 1H), 4.85 (d, J=5.5 Hz, 1H), 6.43 (d, J=5.5 Hz, 1H), 7.19 (m, 2H), 7.35 (dd, J=2 and 9 Hz, 1H), 7.37(d, J=2 Hz, 1H), 7.62 (d, J=9 Hz, 1H), 7.94 (d J=2 Hz, 1H), 8.51(d, J=5.5 Hz, 1H).

EXAMPLE 92 trans-N$_1$-(7-Chloro-quinolin-4-yl)-N$_4$-[2-(4-methoxy-phenyl)-ethyl]-cyclohexane-1,4-diamine dihydrochloride Analogously to Example 88 using 4-methoxyphenethylamine. Yield: 48% of white crystals (from methanol/ether), m.p. 220° C.

ISP mass spectrum: peaks at 410 ((M+H)$^+$, 100%); $^1$H NMR of the free base in CDCl$_3$, δ (ppm): 1.29 (br, 5H), 2.05 (br, 2H), 2.22 (br, 2H), 2.55 (br, 1H), 2.77 (m, 2H), 2.88 (m, 2H), 3.50 (br, 1H), 3.80 (s, 3H), 4.77 (d, 1H), 6.42 (d, J=5.5 Hz, 1H), 6.85 (d, J=8.5 Hz, 2H), 7.14 (d, J=8.5 Hz, 2H), 7.35 (dd, J=2 and 9 Hz, 1H), 7.61 (d, J=9 Hz, 1H), 7.94 (d, J=2 Hz, 1H), 8.52 (d, J=5.5 Hz, 1H).

EXAMPLE 93 trans-N$_1$-(7-Chloro-quinolin-4-yl)-N$_4$-[2-(4-nitro-phenyl)-ethyl]-cyclohexane-1,4-diamine dihydrochloride Analogously to Example 88 using 4-nitrophenethylamine. Yield: 50% of white crystals (from methanol/diethyl ether), m.p. 205° C.

EI mass spectrum: peaks at 424 (M$^+$, 8%), 407 (M-OH, 100%), 288 (44%), 259 (72%), 179 (48%); $^1$H NMR of the free base in CDCl$_3$ δ (ppm) 1.3 (m, 4H), 2.06 (br, 2H), 2.25 (br, 2H), 2.56 (br, 1H), 2.95 (m, 5H), 3.50 (br, 1H), 4.78 (d, 1H), 6.42 (d, J=5.4 Hz, 1H), 7.38 (m, 3H), 7.61 (d, J=9 Hz, 1H), 7.95 (d, J=2 Hz, 1H), 8.17 (d, 2H), 8.52 (d, J=5.4 Hz, 1H).

EXAMPLE 94 trans-N$_1$-(7-Chloro-quinolin-4-yl)-N$_4$-[2-(3,5-dimethoxy-phenyl)-ethyl]-cyclohexane-1,4-diamine dihydrochloride Analogously to Example 88 using 3,5-dimethoxyphenethylamine. Yield: 45% of white crystals (from methanol/diethyl ether), m.p. 210° C.

EI mass spectrum: peaks at 439 (M$^+$, 8%), 288 (100%), 259 (50%), 179 (20%); $^1$H NMR of the free base in CDCl$_3$ δ (ppm): 1.32 (m, 4H), 2.06 (br, 2H), 2.25 (br, 2H), 2.56 (br, 1H), 2.78 (m, 2H), 2.94 (m, 2H), 3.50 (br, 1H), 3.79 (s, 6H), 4.78 (d, 1H), 6.40 (m, 4H), 7.26(dd, J=2 and 9 Hz, 1H), 7.61 (d,J=9 Hz, 1H), 7.95 (d, J=2 Hz, 1H), 8.52 (d, J=5.4 Hz, 1H).

EXAMPLE 95 trans-N$_1$-(2-Benzo[1,3]dioxol-5-yl-ethyl)-N$_4$-(7-chloro-quinolin-4-yl)-cyclohexane-1,4-diamine dihydrochloride Analogously to Example 88 using 3,4-methylenedioxyphenethylamine. Yield: 59% of white crystals (from methanol/diethyl ether), m.p. 215° C.

EI mass spectrum: peaks at 423 (M$^+$, 8%), 388 (M-Cl, 8%), 288 (100%), 259 (68%); $^1$H NMR of the free base in CDCl$_3$ δ (ppm): 1.3 (m, 5H), 2.06 (br, 2H), 2.25 (br, 2H), 2.56 (br, 1H), 2.74 (m, 2H), 2.87 (m, 2H), 3.48 (br, 1H), 4.78 (d, 1H), 5.94 (s, 2H), 6.43 (d, J=5.4 Hz, 1H), 6.42 (m, 3H), 7.22 (m, 4H), 7.35 (dd, J=2 and 9 Hz, 1H), 7.61 (d, J=9 Hz, 1H), 7.95 (d, J=2 Hz, 1H), (d, J=5.4 Hz, 1H).

EXAMPLE 96 trans-$N_1$-[2-(3-Chloro-phenyl)-ethyl]-$N_4$-(7-chloro-quinolin-4-yl)-cyclohexane-1,4-diamine dihydrochloride Analogously to Example 88 using 2-(3-chlorophenyl)ethylamine. Yield: 57% of white crystals (from methanol/diethyl ether), m.p. 249° C.

EI mass spectrum: peaks at 414 (M$^+$, 5%), 288 (100%), 259 (48%); $^1$H NMR of the free base in CDCl$_3$ δ (ppm): 1.0–1.5 (m, 4H), 2.07 (br, 2H), 2.23 (br, 2H), 2.55 (br, 1H), 2.80 (m, 2H), 2.90 (m, 2H), 3.50 (br, 1H), 4.78 (d, 1H), 6.43 (d, J=5.4 Hz, 1H), 7.11 (m, 1H), 7.22 (m, 4H), 7.35 (dd, J=2 and 9 Hz, 1H), 7.62 (d, J=9 Hz, 1H), 7.95 (d, J=2 Hz, 1H), 8.52 (d, J=5.4 Hz, 1H).

EXAMPLE 97 trans-$N_1$-(7-Chloro-quinolin-4-yl)-$N_4$-[2-(2,5-dimethoxy-phenyl)-ethyl]-cyclohexane-1,4-diamine dihydrochloride Analogously to Example 88 using 2,5-dimethoxyphenethylamine. Yield: 46% of white crystals (from methanol/diethyl ether), m.p. 227° C.

EI mass spectrum: peaks at 439 (M$^+$, 8%), 288 (100%), 259 (84%), 152 (92%); $^1$H NMR of the free base in CDCl$_3$ δ (ppm): 1.2–1.6 (m, 5H), 2.08 (br, 2H), 2.25 (br, 2H), 2.58 (br, 1H), 2.84 (m, 4H), 3.50 (br, 1H), 3.77 (s, 3H), 3.79 (s, 3H), 4.78 (d, 1H), 6.43 (d,J=5.4 Hz, 1H), 6.77 (m, 3H), 7.36 (dd,J=2 and 9 Hz, 1H), 7.60 (d,J=9 Hz, 1H), 7.95 (d,J=2 Hz, 1H), 8.52 (d,J=5.4 Hz, 1H).

EXAMPLE 98 trans-$N_1$-(7-Chloro-quinolin-4-yl)-$N_4$-[2-(4-phenoxy-phenyl)-ethyl]-cyclohexane-1,4-diamine dihydrochloride Analogously to Example 88 using 4-phenoxyphenethylamine. Yield: 53% of white crystals (from methanol/diethyl ether), m.p. >250° C.

EI mass spectrum: peaks at 471 ((M-H)$^+$, 2%), 288 (100%), 259 (44%); $^1$H NMR of the free base in CDCl$_3$ δ (ppm): 1.35 (m, 4H), 1.55 (br, 1H), 2.10 (br, 2H), 2.25 (br, 2H), 2.64 (br, 1H), 2.84 (m, 2H), 2.96 (m, 2H), 3.50 (br, 1H), 4.84 (d, 2H), 6.43 (d, J=5.5, 1H), 6.9–7.4 (m, 10H), 7.72 (d, J=9, 1H), 7.96 (d, J=2, 1H), 8.52 (d, J=5.4, 1H).

EXAMPLE 99 trans-$N_1$-(7-Chloro-quinolin-4-yl)-$N_4$-[2-(3,4-dichloro-phenyl)-ethyl]-cyclohexane-1,4-diamine dihydrochloride Analogously to Example 88 using 3,4-dichlorophenethylamine. Yield: 20% of white crystals (from methanol/diethyl ether), m.p. >250° C.

ISP mass spectrum: peaks at 450.2 ((M+H)$^+$, 10%), 276.3 (23%), 225.9 (100%); $^1$H NMR of the free base in DMSO-d$_6$ δ (ppm): 1.63 (br, 4H), 2.00 (br, 2H), 2.20 (br, 2H), 3.0–3.4 (m, 5H), 3.8 (br, 1H), 7.06 (d, J=7 Hz, 1H), 7.28 (dd, J=2 and 8 Hz, 1H), 7.61 (m, 2H), 7.76 (dd, J=2 and 10 Hz, 1H), 8.08 (d, J=2 Hz, 1H), 8.54 (d, J=7 Hz, 1H), 8.76 (d J=10 Hz, 1H), 9.08 (d, J=8 Hz, 1H), 9.34 (br, 2H), 14.4 (br, 1H).

EXAMPLE 100 trans $N_1$-(7-Chloro-quinolin-4-yl)-$N_4$-(4-methoxy-benzyl)-cyclohexane-1,4-diamine dihydrochloride Analogously to Example 88 using 4-methoxybenzylamine. Yield: 20% of beige crystals (from methanol/ether). M.p. >250° C.

ISP mass spectrum: peaks at 396 ((M+H)$^+$, 85%), 276 (100%); $^1$H-NMR in DMSO-d$_6$, δ (ppm): 1.50 (br, 4H), 2.20 (br, 4H), 3.10 (br, 1H), 3.60 (br, 1H), 3.77 (s, 3H), 4.10 (br, 2H), 6.62 (d, J=7.5 Hz, 1H), 7.00 (d, J=10 Hz, 2H), 7.15 (d, 1H), 7.46 (dd, J=2 and 12 Hz, 1H), 7.51 (d, J=10 Hz, 2H), 7.60 (d, J=2 Hz, 1H), 8.37 (d, J=12 Hz, 1H), 8.40 (d, J=7.5 Hz, 1H).

EXAMPLE 101 trans-$N_1$-(7-Chloro-quinolin-4-yl)-$N_4$-[2-(2,6-dichloro-phenyl)-ethyl]-cyclohexane-1,4-diamine dihydrochloride Analogously to Example 88 using 2,6-dichlorophenethylamine. Yield: 38% of white crystals (from methanol-ether). m.p. >250° C.

ISP mass spectrum: peaks at 448 (M$^+$, 35%), 276 (35%), 225 (100%); $^1$H-NMR of the free base in DMSO-d$_6$, δ (ppm): 1.46 (br, 4H), 2.11 (br, 4H), 2.99 (m, 3H), 3.21 (br, 4H), 3.55 (br, 1H), 6.58 (d, J=5.5 Hz, 1H), 7.02 (d, 1H), 7.33 (t, J=8.5, Hz, 1H), 7.44 (dd, J=2 and 9 Hz, 1H), 7.50 (d, J=8.5 Hz, 2H), 7.77 (d, J=2 Hz, 1H), 8.35 (d, J=9 Hz, 1H), 8.39 (d, J=5.5 Hz, 1H).

EXAMPLE 102 trans $N_1$-(7-Chloro-quinolin-4-yl)-$N_4$-(3,4-dichloro-benzyl)-cyclohexane-1,4-diamine dihydrochloride Analogously to Example 88 using 3,4-dichlorobenzylamine. Yield: 50% of white crystals (from methanol/ether). M.p.>250° C.

ISP mass spectrum: peaks at 434 (M$^+$, 35%), 276 (100%); $^1$H-NMR of the free base in DMSO-d$_6$, δ (ppm): 1.32 (br, 4H), 1.98 (br, 4H), 3.40 (br, 1H), 3.80 (s, 2H), 6.53 (d, J=5.5 Hz, 1H), 6.90 (d, 1H), 7.38 (dd, J=2 and 9.5 Hz, 1H), 7.41 (dd, J=2 and 8 Hz, 1H), 7.58 (d, J=8 Hz, 1H), 7.66 (d, J=2 Hz, 1H), 7.76 (d, J=2 Hz, 1H), 8.32 (d, J=9.5 Hz, 1H), 8.37 (d, J=5.5 Hz, 1H).

EXAMPLE 103 trans-$N_1$-Benzo[1,3]dioxol-5-ylmethyl-$N_4$-(7-chloro-quinolin-4-yl)-cyclohexane-1,4-diamine dihydrochloride Analogously to EXAMPLE 88 using piperonylamine. Yield: 41% of white crystals (from methanol/ether). M.p.>250° C.

ISP mass spectrum: peaks at 410 ((M+H)$^+$, 35%), 278 (55%), 276 (100%); $^1$H-NMR of the free base in CDCl$_3$ δ (ppm): 1.34 (br, 4H), 2.08 (br, 4H), 2.60 (br, 1H), 3.55 (br, 1H), 3,77 (s, 2H), 4.80 (d, 1H), 5.95 (s, 2H), 6.43 (d, J=5.5 Hz, 1H), 6.81 (br, 4H), 7.35 (dd, J=2 and 9 Hz, 1H), 7.61 (d, J=9 Hz, 1H), 7.94 (d, J=2 Hz, 1H), 8.52 (d, J=5.5 Hz, 1H).

EXAMPLE 104 trans-4-{2-[4-(7-Chloro-quinolin-4-ylamino)-cyclohexylamino]-ethyl}-2-methoxy-phenol dihydrochloride Analogously to Example 88 using 4-hydroxy-3-methoxyphenethylamine. Yield: 14% of beige crystals (from methanol/ether). M.p.: 209° C.

ISP mass spectrum: peaks at 426 (M$^+$, 100%), 428 (M+2H$^+$, 35%); $^1$H-NMR of the free base in DMSO-d$_6$, δ (ppm): 1.50–2.00 (m, 8H), 2.65 (br, 2H), 2.70–3.00 (m, 3H), 3.60 (br, 1H), 3.74 (s, 3H), 6.50 (d, J=5.5 Hz, 1H), 6.61 (dd, J=2 and 8 Hz, 1H), 6.68 (d, J=8 Hz, 1 H), 6.78 (d, J=2 Hz, 1H), 6.85 (d, 1H), 7.42 (dd, J=2 and 9 Hz, 1H), 7.76 (d, J=2 Hz, 1H), 8.37 (d, J=5.5 Hz, 1H), 8.40 (d, J=9 Hz, 1H), 8.72 (s, 1H).

EXAMPLE 105 trans-$N_1$-(7-Chloro-quinolin-4-yl)-$N_4$-[2-(2,3-dimethoxy-phenyl)-ethyl]-cyclohexane-1,4-diamine dihydrochloride Analogously to Example 88 using 2,3-dimethoxyphenethylamine. Yield: 25% of beige crystals (from methanol/ether). M.p: 284° C.

ISP mass spectrum: peaks at 440 (M$^+$, 100%), 442 (M+2H$^+$, 35%); $^1$H-NMR of the free base in CDCl$_3$ δ (ppm): 1.85 (br, 4H), 2.10 (br, 2H), 2.30 (br, 2H), 2,65 (br, 1H), 2.96 (br, 4H), 3.49 (br, 1H), 3.85 (s, 3H), 3.87 (s, 3H), 4.80 (d, 1H), 6.44 (d, J=6 Hz, 1H), 6.85 (m, 2H), 7.02 (m, 1H), 7.35 (dd, J=2 and 10 Hz, 1H), 7.62 (d, J=10 Hz, 1H), 7.95 (d, J=2 Hz, 1H), 8.53 (d, J=6 Hz, 1 H).

EXAMPLE 106 trans-$N_1$-(7-Chloro-quinolin-4-yl)-$N_4$-(3,5-dimethoxy-benzyl)-cyclohexane-1,4-diamine Analogously to Example 88 using 3,5-dimethoxybenzylamine. Yield: 50% of white crystals (from methylene chloride/ether). M.p:150° C.

ISP mass spectrum: peaks at 426(M$^+$, 100%), 428 (M+2H$^+$, 55%); $^1$H-NMR of the free base in CDCl$_3$, δ (ppm): 1.33 (br, 4H), 1.99 (br, 4H), 3.45 (br, 1H), 3.73 (s, 6H), 3.73 (s, 2H), 6.36 (m, 1H), 6.53 (d, J=5Hz, 1H), 6.55 (d, 2H), 6.89 (d, 1 H), 7.41 (dd, J=2 and 9 Hz, 1H), 7.76 (d, J=2 Hz), 1H), 8.31(d, J=9 Hz, 1H), 8.39 (d, J=5 Hz, 1H).

EXAMPLE 107 trans-$N_1$-(3-Chloro-benzyl)-$N_4$-(7-chloro-quinolin-4-yl)-cyclohexane-1,4-diamine dihydrochloride Analogously to Example 88 using 3-chlorobenzylamine. Yield: 50% of white crystals (from methanol/ether). M.p.>280° C.

ISP mass spectrum: peaks at 400 (M$^+$, 100%), 402 (M+2H$^+$, 90%); $^1$H-NMR of the free base in CDCl$_3$, δ (ppm): 1.25 (m, 4H), 2.08 (br, 2H), 2.23 (br, 2H), 2.60 (br, 1H), 3.49 (br, 1H), 3.83 (s, 2H), 4.90 (d, 1H), 6.44 (d, J=5.5 Hz, 1H), 7.25 (m, 3H), 7.35 (m, 1 H), 7.35 (dd, J=2 and 9 Hz, 1H), 7.62 (d, J=9 Hz, 1H), 7.95 (d, J=2 Hz, 1H), 8.51 (d, J=5.5 Hz, 1H).

EXAMPLE 108 trans $N_1$-(7-Chloro-quinolin-4-yl)-$N_4$-(2,4,6-trimethoxy-benzyl)-cyclohexane-1,4-diamine dihydrochloride Analogously to Example 88 using 2,4,6-trimethoxybenzylamine. Yield: 26% of white crystals (from methanol/ether). M.p. 271° C.

ISP mass spectrum: peaks at 456 (M$^+$, 100%), 458 (M+2H$^+$, 35%); $^1$H-NMR of the free base in CDCl$_3$, δ (ppm): 1.32 (br, 4H), 2.08 (br, 2H), 2.25 (br, 2H), 2.48 (br, 1H), 3.48 (br, 1H), 3.81 (s, 9H), 3.81 (s, 2H), 4.78 (d, 1H), 6.13 (m, 3H), 6.44 (d, J=5.5 Hz, 1H), 7.34 (dd, J=2 and 9 Hz, 1H), 7.60 (d, J=9 Hz, 1H), 7.94 (d, J=2Hz, 1H), 8.51 (d, J=5.5 Hz, 1H).

EXAMPLE 109 trans-$N_1$-(7-Chloro-quinolin-4-yl)-$N_4$-(2,4-dichloro-benzyl)-cyclohexane-1,4-diamine dihydrochloride Analogously to Example 88 using 2,4-dichlorobenzylamine. Yield 53% of white crystals (from methanol/ether). M.p. 232° C.

ISP mass spectrum: peaks at 434 (M$^+$, 100%), 436 ((M+2H)$^+$, 85%); $^1$H-NMR of the free base in DMSO-d$_6$, δ (ppm): 1.23–1.50 (m, 4H), 1.98 (br, 4H), 2.48 (br, 2H), 3.50 (br, 1H), 3.60 (s, 2H), 6.52 (d, J=5.5 Hz, 1H), 6.85 (d, 1H), 7.41 (d, J=6.5 Hz, 1H), 7.42 (dd, J=2 and 8.5 Hz, 1H), 7.57 (d, J=2 Hz, 1H), 7.61 (d, J=6.5 Hz, 1H), 7.75 (d, J=2 Hz, 1H), 8.33 (d, J=8.5 Hz, 1H), 8.36 (d, J=5.5 Hz, 1H).

EXAMPLE 110 trans-$N_1$-(7-Chloro-quinolin-4-yl)-$N_4$-(3,4-dimethoxy-benzyl)-cyclohexane-1,4-diamine dihydrochloride Analogously to Example 88 using veratrylamine. Yield 22% of white crystals (from methanol/ether). M.p.>270° C.

ISP mass spectrum: peaks at 426 ((M+H)$^+$, 100%); $^1$H-NMR of the free base in CDCl$_3$, δ (ppm): 1.25–1.50 (m, 4H), 2.10 (br, 2H), 2.28 (br, 2H), 2.60 (br,1H), 3.49 (br,1H), 3.80 (s, 2H), 3.87 (s, 3H), 3.90 (s,3H), 4.80 (d,1 H), 6.44 (d, J=5.5 Hz, 1 H), 6.84 (m, 2H), 6.91 (d, J=2 Hz, 1H), 7.35 (dd, J=2 and 9 Hz, 1H), 7.61 (d, J=9 Hz, 1H), 7.95 (d, J=2 Hz, 1H), 8.52 (d, J=5.5 Hz, 1 H).

EXAMPLE 111 trans-$N_1$ (7-Chloro-quinolin-4-yl)-$N_4$-(2,4-dimethoxy-benzyl)-cyclohexane-1,4-diamine dihydrochloride Analogously to Example 88 using 2,4-dimethoxybenzylamine. Yield 20% of white crystals (from methanol/ether). M.p.>270° C.

EI mass spectrum: peaks at 426 (M$^+$, 2%), 274 (100%), 151 (90%); $^1$H-NMR of the free base in DMSO-d$_6$, δ (ppm): 1.40 (m, 4H), 2.00 (br, 4H), 2.50 (br, 1H), 3.48 (br, 1H), 3.73 (s, 2H), 3.75 (s, 3H), 3.79 (s, 3H), 6.50 (m, 3H), 6.91 (d, 1H), 7.24 (d, J=8 Hz, 1H), 7.42 (dd, J=2 and 9.5 Hz, 1H), 7.76 (d, J=2 Hz, 1H), 8.32 (d, J=9.5 Hz, 1H), 8.37 (d, J=5 Hz, 1H).

EXAMPLE 112 trans-$N_1$-(7-Chloro-quinolin-4-yl)-$N_4$-(3,4,5-trimethoxy-benzyl)-cyclohexane-1,4-diamine dihydrochloride Analogously to Example 88 using 3,4,5-trimethoxybenzylamine. Yield 36% of white crystals (from methanol/ether). M.p.>250° C.

ISP mass spectrum: peaks at 456 ((M+H)$^+$, 100%); $^1$H-NMR of the free base in CDCl$_3$, δ (ppm): 1.37 (br, 4H), 2.15 (br, 2H), 2.30 (br, 2H), 2.70 (br, 1H), 3.50 (br, 1H), 3.80 (s, 2H), 3.83 (s, 3H), 3.88 (s, 6H), 4.80 (d, 1H), 6.44 (d, J=5.5 Hz, 1H), 6.58 (s, 2H), 7.35 (dd, J=2 and 10 Hz, 1H), 7.62 (d, J=10 Hz, 1H), 7.95 (d, J=2 Hz, 1H), 8.52 (d, J=5.5 Hz, 1H).

EXAMPLE 113 trans-$N_1$-(7-Chloro-quinolin-4-yl)-$N_4$-(4-dimethylamino-benzyl)-cyclohexane-1,4-diamine trihydrochloride Analogously to Example 88 using 4-dimethylaminobenzylamine. Yield 20% of beige crystals (from methanol/ether). Dec. from 240° C.

ISP mass spectrum: peaks at 409 ((M+H)+, 75%), 276 (75%); 1 H-NMR of the free base in CDCl$_3$, δ (ppm): 1.25–150 (m, 4H), 2.20 (br, 4H), 2.60 (br, 1H), 2.93 (s, 6H), 3.50 (br, 1H), 3.76 (s, 2H), 4.80 (d, 1H), 6.43 (d, J=5.5 Hz, 1H), 6.72 (d, J=9 Hz, 2H), 7.22 (d, J=9 Hz, 2H), 7.35 (dd, J=2 and 9 Hz, 1H), 7.61 (d, J=9 Hz, 1H), 7.95 (d, J=2 Hz, 1H), 8.52 (d, J=5.5 Hz, 1H).

EXAMPLE 114 trans-N$_1$-(7-Chloro-quinolin-4-yl)-N$_4$-(2,6-difluoro-benzyl)-cyclohexane-1,4-diamine dihydrochloride Analogously to Example 88 using 2,6-difluorobenzylamine. Yield 42% of white crystals (from methanol/ether). M.p. 262° C.

ISP mass spectrum: peaks at 402 ((M+H)+, 100%), 276 (95%), 202 (½(M+2H)$^{2+}$; 95%); $^1$H-NMR of the free base in CDCl$_3$, δ (ppm): 1.35 (m, 4H), 1.75 (br, 1H), 2.10 (br, 2H), 2.25 (br, 2H), 2.55 (br, 1H), 3.49 (br, 1H), 3.95 (s, 2H), 4.84 (d, br, 1H), 6.44 (d, J=5.5 Hz, 1H), 6.70 (m, 2H), 7.25 (m, 1 H), 7.35 (dd, J=2 and 9 Hz, 1 H), 7.61 (d, J=9 Hz, 1 H), 7.95 (d, J=2 Hz, 1H), 8.51 (d, J=5.5 Hz, 1H).

EXAMPLE 115 trans-N$_1$-(7-Chloro-quinolin-4-yl)-N$_4$-(2-pyridin-2-yl-ethyl)-cyclohexane-1,4-diamine trihydrochloride Analogously to Example 88 using 2-(2-aminoethyl)-pyridine. Yield 26% of white crystals (from methanol/ether). M.p. 225° C.

EI mass spectrum: peaks at 380 (M+, 20%), 288 (20%), 259 (35%), 179 (85%), 93 (100%); $^1$H-NMR of the free base in CDCl$_3$, δ (ppm): 1.21–1.43 (m, 4H), 2.09 (br, 2H), 2.22 (br, 2H), 2.60 (br, 1H), 3.04 (AB system, 4H), 3.50 (br, 1H), 4.81 (d, br, 1H), 6.43 (d, J=5.5 Hz, 1H), 6.92 (d, J=9 Hz, 2H), 7.21 (m, 2H), 7.35 (dd, J=2 and 9 Hz, 1 H), 7.60 (m, 1H), 7.95 (d, J=2 Hz, 1H), 8.52 (d, J=9 Hz, 1H), 8.55 (d, J=5.5 Hz, 1H).

EXAMPLE 116 trans-N$_1$-(1H-Benzimidazol-2-ylmethyl)-N$_4$-(7-chloro-quinolin-4-yl)-cyclohexane-1,4-diamine trihydrochloride Analogously to Example 88 using (2-aminoethyl)-benzimidazole. Yield 22% of white crystals (from methanol/ether). M.p.>250° C.

ISP mass spectrum: peaks at 406 ((M+H)+, 55%), 276 (50%), 224 (35%), 204 (½(M+2H)$^{2+}$; 100%); $^1$H-NMR of the free base in d$_6$-DMSO, δ (ppm): 1.18–1.50 (m, 4H), 2.01 (d, br, 4H), 3.64 (br, 1H), 4.01 (s, 2H), 6.53 (d, J=5.5 Hz, 1H), 6.92 (d, J=9 Hz, 2H), 7.13 (m, 2H), 7.42 (dd, J=2 and 9 Hz, 1H), 7.50 (br, 1H), 7.75 (d, J=2 Hz, 1H), 8.31 (d, J=9 Hz, 1H), 8.37 (d, J=5.5 Hz, 1H), 12.2 (br, 1H).

EXAMPLE 117 trans-N$_1$-(7-Chloro-quinolin-4-yl)-N$_4$-[2-(1H-indol-3-yl)-ethyl]-cyclohexane-1,4-diamine dihydrochloride Analogously to Example 88 using tryptamine. Yield 19% of white crystals (from methanol/ether). M.p.>250° C.

ISP mass spectrum: peaks at 419 ((M+H)+, 40%), 276 (100%);$^1$H-NMR of the free base in d$_6$-DMSO, δ (ppm): 1.12–1.50 (m, 4H), 1.99 (br, 4H), 3.08–3.64 (m, 4H), 4.42 (m, 2H), 6.51 (d, J=5.5,Hz, 1H), 6.88–7.12 (m, 3H), 6.72 (d, J=9 Hz, 2H), 7.17 (d, J=2 Hz, 1H), 7.33 (d, J=8 Hz, 1H), 7.42 (dd, J=2 and 9 Hz, 1H), 7.52 (d, J=7.5 Hz, 1H), 7.76 (d, J=2 Hz, 1H), 8.31 (s, 1H), 8.36 (d, J=5.5 Hz, 1H), 10.80 (s, br, 1H).

The intermediates used in the foregoing Examples were in part accessible according to known and described procedures or in part were prepared in the following manner:

EXAMPLE 118

(2R)-N$_1$-(7-Chloro-quinolin-4-yl)-1,2-propane-diamine (starting material for Example 1)

2.9 g of (S)-2-amino-1-chloro-N-(7-chloro-quinolin-4-yl)-propane were held at 110° C./40 bar in 30 ml of methanol and 30 ml of liquid ammonia in a bomb tube for 20 hrs. After cooling the ammonia was carefully allowed to evaporate and the residue was then poured into 100 ml of saturated sodium chloride solution and extracted twice with 100 ml of dichloromethane. The organic phase was dried over sodium sulphate and evaporated. The crude product was chromatographed on neutral aluminium oxide in dichloromethane/methanol 10:1 and then crystallized from dichloromethane/toluene. 1.9 g (80%) of (2R)-N$_1$-(7-chloro-chinolin-4-yl)-1,2-propane-diamine were obtained as white crystals; m.p. 145° C.

EXAMPLE 119

(S)-N$_2$-(7-Chloro-quinolin-4-yl)-1,2-propane-diaminedihydrochloride (starting material for Example 2)

Step 1

23 g of L-alaninol and 57.4 g of 4,7-dichloroquinoline were held at 150° C. in 100 ml of 1-methyl-2-pyrrolidone for 6 hrs. After cooling the reaction mixture was poured into 500 ml of cold 2N HCl and extracted three times with 200 ml of dichloromethane. The acidic-aqueous phase was made basic with 28% NaOH, and the product separated. After stirring in an ice bath for 30 min. the product was filtered off and then recrystallized from 300 ml of 2-propanol/150 ml of ethanol. There were obtained 51.2 g (74%) of (S)-2-amino-N-(7-chloro-quinolin-4-yl)-1-propanol; white crystals, m.p. 225° C., [α]$_D$=+35° (c=1.0, MeOH).

$^1$H-NMR (250 MHz) in d$_6$-DMSO, signals at δ (ppm): 1.24 (d, J=6.4 Hz, 3H), 3.45 (m, 1H), 3.58 (m, 1H), 3.73 (m, 1H), 4.87 (t, J=5.6 Hz, 1H), 6.53 (d, J=7 Hz, 1H), 6.84 (d, J=7.7 Hz, 1H), 7.44 (dd, J=2 and 9 Hz, 1H), 7.78 (d, J=2 Hz, 1H), 8.35 (d, J=7 Hz, 1H), 8.39 (d, J=9 Hz, 1H).

Step 2

27.3 g of (S)-2-amino-N-(7-chloro-quinolin-4-yl)-1-propanol were suspended in 270 ml of chloroform. Then, a solution of 72 ml of thionyl chloride in 70 ml of chloroform was added dropwise thereto while cooling with ice over 30 min., with the temperature not exceeding 25° C. Subsequently, the mixture was stirred at room temperature for a further 30 min. and at 70° C. for 90 min. The reaction mixture was cooled and evaporated, then treated with toluene and again evaporated. The resulting foam was dissolved in 500 ml of ethanol while warming, filtered and concentrated to about 300 ml, whereupon crystallization occured. There were obtained 31.6 g (94%) of (S)-2-amino-1-chloro-N-(7-chloro-quinolin-4-yl)-propanehydrochloride; m.p. 210° C., [α]$_D$=+90° (c=1.0, MeOH).

$^1$H-NMR (250 MHz) in d$_6$-DMSO, signals at δ (ppm): 1.41 (d, J=6.5 Hz, 3H), 3.88–4.06 (m, 2H), 4.48 (m, 1H), 7.03 (d, J=7.3 Hz, 1H), 7.79 (dd, J=2 Hz and 9 Hz, 1H), 8.15

(d, J=2 Hz, 1H), 8.59 (d, J=7.3 Hz, 1H), 8.89 (d, J=9 Hz 1H), 9.44 (d, J=8.4 Hz, 1H), 14.66 (s, 1H).

Step 3:

7.1 g of (S)-2-amino-N-(7-chloro-quinolin-4-yl)-1-propanol were suspended in 70 ml of dichloromethane under argon, treated with 6.2 ml of triethylamine and then cooled in ice. 3.2 ml of methanesulphonyl chloride were added dropwise thereto at 5° C. over 10 min. and the mixture was left to warm for 1 h., diluted with 70 ml of dichloromethane and extracted twice with 100 ml of water. After drying and evaporation the crude product was dissolved in 70 ml of N,N-dimethylformamide and stirred at 70° C. with 2 g of sodium azide for 3 h. After cooling the mixture was extracted twice with 200 ml of ethyl acetate and twice with 200 ml of water. The crude product was chromatographed on silica gel in ethyl acetate and crystallized from 15 ml of hot ethyl acetate and 30 ml of hexane. There were obtained 4.3 g (55%) of (S)-2-amino-1-azido-N-(7-chloro-quinolin-4-yl)-propane; white crystals; m.p. 137° C., $[\alpha]_D$=+130° (c=1.0, MeOH).

$^1$H-NMR (250 MHz) in $d_6$-CDCl$_3$, signals at δ (ppm): 1.41 (d, J=6.5 Hz, 3H), 3.49–3.65 (m 2H), 3.96 (m, 1H), 5.00 (d, J=10 Hz, 1H), 6.44 (d, J=7.3 Hz, 1H), 7.38 (dd, J=2 Hz and 9 Hz, 1H), 7.68 (d, J=9 Hz, 1H), 7.97 (d, J=2 Hz, 1H), 8.56 (d, J=7.3 Hz, 1H).

Step 4:

2 g of (S)-2-amino-1-azido-N-(7-chloro-quinolin-4-yl)-propane were dissolved in 38 ml of methanol, then 5.3 ml of triethylamine and 3.8 ml of propane-1,3-dithiol were added and the mixture was stirred at room temperature for 72 hrs. The reaction mixture was evaporated and dried in a high vacuum for a further 4 h. For crystallization, the resulting oil was triturated with 15 ml of toluene. 0.98 g (54%) of white crystals, m.p. 113° C., was obtained. For the preparation of the hydrochloride, 0.5 g of free base was dissolved in 10 ml of acetone and then treated with 2.3 ml of 2N HCl. There was obtained 0.63 g (96%) (S)-N$_2$-(7-chloro-quinolin-4-yl)-1,2-propanediamine-dihydrochloride; white crystals; m.p. 210° C., $[\alpha]_D$=+104° (c=1.0, MeOH).

$^1$H-NMR (250 MHz) in $d_6$-DMSO, signals at δ (ppm): 1.38 (d, J=6.5 Hz, 3H), 3.16 (m, 1H), 3.36 (m, 1H), 4.51 (m, 1H), 7.01 (d, J=7 Hz, 1H), 7.76 (dd, J=2 Hz and 9 Hz, 1H), 8.52 (m, 3H), 8.61 (d, J=7 Hz, 1H), 8.97 (d, J=9 Hz, 1H), 9.47 (d, J=9 Hz, 1H), 14.7 (br, s, 1H).

EXAMPLE 120

N$_1$-(7-Chloro-quinolin-4-yl)-2-methyl-propane-1,2-diamine (starting material for Examples 3–59).

198 g of 4,7-dichloroquinoline, 97 g of 1,2-diamino-2-methyl-propane and 101 g of triethylamine were stirred in 1 l of N-methyl-2-pyrrolidone at 150° C. under argon for 5 hours. The solvent was evaporated in a vacuum and the residue was taken up in 1 l of water. The pH was adjusted to 1 using 220 ml of 25% hydrochloric acid and the mixture was diluted with 6 l of water and extracted four times with 0.5 l of ethyl acetate each time. The clear aqueous solution was treated with about 900 g of KOH, whereby the pH rose to 14 and the product separated in crystalline form. This was filtered off under suction, rinsed with about 3 l of water and, for further purification, recrystallized from 4 l of acetonitrile. There were obtained 126.7 g (73%) of N$_1$-(7-chloro-quinolin-4-yl)-2-methyl-propane-1,2-diamine, m.p. 182–184° C.

$^1$H-NMR in CDCl$_3$, δ (ppm): 1.25 (m, 2H), 1.28 (s, 6H), 3.08 (d, J=5 Hz, 1H), 6.37 (d, J=6 Hz, 1H), 7.37 (dd, J=2 Hz and 8 Hz, 1H), 7.76 (d, J=8 Hz, 1H), 7.95 (d, J=2 Hz, 1H), 8.51 (d, J=6 Hz, 1H).

EXAMPLE 121

(1S,2S)-N$_1$-(7-Chloro-quinolin-4-yl)-cyclohexane-1,2-diamine (starting material for Examples 60–67)

13.6 g of (1S,2S)-(+)-1,2-diaminocyclohexane, 23.6 g of 4,7-dichloroquinoline and 16.6 ml of triethylamine were held at 150° C. in 150 ml of 1-methyl-2-pyrrolidone under argon for 16 hrs. The solvent was largely distilled off at 0.1 Torr/80° C. and the residue was triturated with 300 ml of 1.5N HCl. The resulting aqueous suspension was extracted three times with 300 ml of dichloromethane and then made basic with concentrated ammonia, with gum-like clumps separating. The supernatant solution was decanted off and extracted twice with 400 ml of dichloromethane. The crude product obtained from these extracts was purified by two-fold flash chromatography on neutral aluminium oxide (Brockmann activity II) with dichloromethane and dichloromethane/ethanol 30:1. Crystallization was effected from 40 ml of dichloromethane and 60 ml of ethyl acetate by distillation of the former. Yield: 4 g (12%) of (1S,2S)-N-(7-chloro-quinolin-4-yl)-cyclohexane-1,2-diamine; m.p. 160° C., $[\alpha]_D$=+129.30 (MeOH, c=1.0).

EXAMPLE 122 cis-N$_1$-(7-Chloro-quinolin-4-yl)-cyclopentane-1,3-diamine (starting material for Example 68)

29.5 g of cyclopentane-1,3-diamine dihydrobromide [prepared according to O. Diels, J. H. Blom and W. Knoll, Liebigs Ann. 443, 242 (1925)] were held for 6 hours in a heating bath at 180° C. together with 19.8 g of 4,7-dichloroquinoline and 27.8 ml of triethylamine in 100 ml of 1-methyl-2-pyrrolidone. The cooled reaction mixture was poured into 1 l of water and the pH of the mixture was adjusted to 7 using 10% aqueous KOH. The mixture was extracted first with 5 0.5 l portions of ethyl acetate, the pH was increased to 12 using KOH and the mixture was again extracted with 3 0.5 l portions of ethyl acetate. The latter extract yielded, after evaporation of the solvent, 29.9 g of a crude product which, for further purification, was chromatographed on 500 g of silica gel with a dichloromethane-methanol mixture in the ratio by volume 97:3. After a fore-run of 2.5 l, which consisted of a mixture of the product with byproducts, there was obtained in the subsequent 3.75 l of eluate, an almost pure product which, after evaporation of the solvent, was obtained as a yellow oil and which, as such, was used for the further reactions. Yield: 5.1 g of cis-N-(7-chloro-quinolin-4-yl)-cyclopentane-1,3-diamine $^1$H-NMR in DMSO-d$_6$, δ (ppm): 1.44 (m, 2H), 1.71–2.13 (m, 5H), 2.22 (quint., J=6.9 Hz, 1H), 3.34 (m, 1H), 3.97 (m, 1H), 6.46 (d, J=6Hz, 1H), 7.30 (d, J=7.5 Hz), 7.44 (dd, J=2 Hz and 9 Hz, 1H), 7.77 (d, J=2 Hz, 1H), 8.26 (d, J=9 Hz, 1H), 8.39 (d, J=6 Hz, 1H).

EXAMPLE 123 cis-N$_1$-(7-Chloro-quinolin-4-yl)-cyclohexane-1,4-diamine (starting material for Examples 69–87)

Step 1:

trans-N-(7-Chloro-quinolin-4-yl)-4-aminocyclohexanol 414.2 g of 4,7-dichloroquinoline, 380 g of trans-4-amino-cyclohexanol hydrochloride and 255 9 of triethylamine were heated to reflux overnight in 1.05 l of 1-methyl-2-pyrrolidone under an argon atmosphere. After cooling the reaction mixture 3.8 l of water and 380 ml of 28% sodium hydroxide solution were added thereto while stirring and cooling. The separated reaction product was filtered off under suction, washed with water until the wash water was neutral and dried at 100° C./12 mbar. Yield 491 g (84.9%) of trans-N-(7-chloro-quinolin-4-yl)-4-aminocyclohexanol.

Step 2:

trans-N-(7-Chloro-quinolin-4-yl)-4-methanesulphonyloxy-cyclo-hexylamine 447 ml of methanesulphonyl chloride were added portionwise within 20 minutes while cooling with an ice bath to a mixture of 1157 g of trans-N-(7-chloro-quinolin-4-yl)-4-aminocyclohexanol and 868 ml of triethylamine in 6.1 l of dichloromethane. After a clear solution formed transiently the product began to separate. After 2 hours the mixture was filtered and the filtrate was evaporated to dryness. Filter residue and evaporation residue were combined and triturated. in 8 l of water. The mixture was again filtered, washed with a further 8 l of water and thereafter with 4 l of isopropanol and the product obtained was dried at 50° C./12 mbar. Yield: 2028 g (90%) of trans-N-(7-chloro-quinolin-4-yl)-4-methanesulphonyloxy-cyclohexylamine, m.p.: 154–159° C.

Step 3:

cis-N-(7-Chloro-quinolin-4-yl)-cyclohexyl-1,4-diamine 433 g of trans-N-(7-chloro-quinolin-4-yl)-4-methanesulphonyloxy-cyclohexylamine were reacted at 80° C. for 10 hours with 80.7 g of sodium azide in 2.16 l of N,N-dimethylformamide. After cooling to room temperature 2.36 l of ethyl acetate and 2 l of water were added thereto in succession, the pH was adjusted to 9 by the addition of 28% sodium hydroxide solution and the phases were left to separate. The aqueous phase was back-extracted a further seven times with 0.5 l of ethyl acetate each time. The pooled ethyl acetate extracts were combined and evaporated. The evaporation residue crystallized after the addition of 0.5 l of n-hexane. It was filtered off under suction and dried at 40° C./12 mbar. The thus-obtained crude product (256 g) consisted of 78% of trans-N-(7-chloro-quinolin-4-yl)-4-azido-cyclohexylamine (corresponding to 192 g, 53%) in addition to 18% of an elimination product and 7% of unreacted trans-N-(7-chloro-quinolin-4-yl)-4-methanesulphonyloxy-cyclohexylamine.

220 g of this crude product were suspended in 2.5 l of isopropanol. 203 ml of triethylamine, 7.24 ml of 1,3-propanedithiol and 54.8 g of sodium borohydride were added thereto in succession and the mixture was warmed to 40° C. while stirring. After 16 hours a further 54.5 g of sodium borohydride was added thereto. After a total reaction period of 40 hours the mixture was cooled using an ice bath and excess hydride was decomposed by the slow addition of 180 ml of glacial acetic acid. After the hydrogen evolution died away the reaction mixture was evaporated on a rotary evaporator. Then, 0.3 l of methanol was added thereto and the mixture was again evaporated. Addition of methanol and evaporation were repeated a total of 5 times with 0.3 l portions each time. Thereafter, the residue was taken up in 3 l of 3N sodium hydroxide solution and extracted three times with 1 l of dichloromethane each time. The combined dichloromethane phases were then extracted with 1.5 l of water, with the aqueous phase being adjusted to pH 7 by the addition of about 2 l of 1N hydrochloric acid. The extraction was repeated twice with 2 l of water/dil. hydrochloric acid while maintaining this pH. After combining the aqueous extracts the pH was adjusted to 12–13 using 28% sodium hydroxide solution and the product was extracted with 3 1 l portions of ethyl acetate. After evaporation of the solvent pure, crystalline cis-N-(7-chloro-quinolin-4-yl)-cyclohexyl-1,4-diamine remained behind in a yield of 128 g and was used without further purification. It was recrystallized from methanol-diethyl ether (20.6 g from 32 g of crude product in 50 ml of methanol and 400 ml of diethyl ether); m.p. 139–140° C.

$^1$H-NMR in DMSO-d$_6$, δ (ppm): 1.65 (m, 6H), 1.89 (m, 2H), 3.05 (m, 1H), 3.60 (m, 1H), 3.75 (m, 2H), 6.50 (d, J=6.5 Hz, 1H), 6.84 (d, J=7 Hz, 1 H), 7.44 (dd, J=2 Hz and 8.5 Hz, 1H), 7.78 (d, J=2 Hz, 1H), 8.38 (d, J=6.5 Hz, 1H), 8.42 (d, J=8.5 Hz, 1H).

EXAMPLE 124

4-(7-Chloro-quinolin-4-ylamino)-cyclohexanone

Starting material for Examples 88–117 and analogues.

13.6 g of trans-4-(7-chloro-quinolin-4-ylamino)-cyclohexanol (Example 123, step 1) were dissolved in 100 ml of dimethyl sulphoxide and 68 ml of triethylamine and cooled to +10° C. under argon. A solution of 25.5 g of sulphur trioxide-pyridine complex in 100 ml of dimethyl sulphoxide was added dropwise in such a manner that the internal temperature did not exceed +15° C. After stirring for an additional 90 minutes, 800 ml of water were rapidly added dropwise. The emulsion obtained became a filterable suspension after vigourous stirring at +10° C. The filter material was recrystallized from ethanol-ether. Yield: 10.1 g (75%) of beige crystals; dec. 195° C.

EI mass spectrum: peaks at 274 (M$^+$, 65%), 217 (100%). $^1$H-NMR in DMSO-d$_6$, δ (ppm): 1.85 (m, 2H), 2.25 (m, 4H), 2.60 (m, 2H), 4.06 (m, 1H), 6.68 (d, J=7.5 Hz, 1H), 7.05 (d, J=9Hz,1H), 7.46 (dd, J=2 and 10 Hz, 1H), 7.79 (d, J=2 Hz, 1H), 8.36 (d, J=10 Hz, 1H), 8.44 (d, J=9 Hz, 1H).

Any of the compounds described in the foregoing can be formulated as the active ingredient according to methods known per se to give pharmaceutical preparations of the following composition:

| 1. 500 mg tablets | |
|---|---|
| Active ingredient | 500 mg |
| Lactose powd. | 149 mg |
| Polyvinylpyrrolidone | 15 mg |
| Dioctyl sodiumsulphosuccinate | 1 mg |
| Na carboxymethylstarch | 30 mg |
| Magnesium stearate | 5 mg |
| | 700 mg |
| 2. 50 mg tablets | |
| Active ingredient | 50 mg |
| Lactose powd. | 50 mg |
| Microcrystalline cellulose | 82 mg |
| Na carboxymethylstarch | 15 mg |
| | 200 mg |
| 3. 100 mg capsules | |
| Active ingredient | 100.0 mg |
| Lactose powd. | 104.7 mg |
| Corn starch | 70.0 mg |
| Hydroxypropylmethylcellulose | 10.0 mg |
| Dioctyl sodiumsulphosuccinate | 0.3 mg |
| Talc | 12.0 mg |
| Magnesiumstearate | 3.0 mg |
| | 300.0 mg |
| 4. 500 mg suppositories | |
| Active ingredient | 500 mg |
| Suppository mass | ad 2000 mg |
| 5. 100 mg soft gelatine capsules | |
| Active ingredient | 100 mg |
| Medium chain triglyceride | 300 mg |
| | 400 mg |

We claim:
1. A compound of the formula

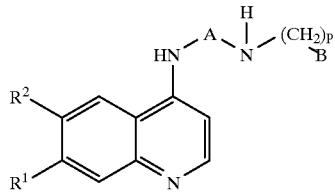

wherein
R¹ is halogen or trifluoromethyl;
R² is selected from the group consisting of hydrogen, halogen and trifluoromethyl;
A is

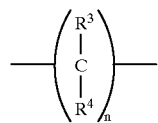

or $(C_5-C_6)$-cycloalkylene
n is 1–4;
R³ and R⁴ are each independently hydrogen or methyl;
p is 1–3;
B is aryl selected from phenyl, phenyl mono-, di-, or tri-substituted by substituent from the group consisting of halogen, hydroxy, lower alkyl, lower alkoxy, trifluoromethyl, cyano, di-lower alkylamino or their N-oxides, phenyloxy, phenyl, and methylsuphanyl, naphthyl, benzo[1,3]dioxol, or monocyclic aromatic heterocycle with 1 or 2 heteroatoms selected from N and O;
as well as pharmaceutically acceptable salts of basic compounds of formula I, wherein when A is —(C(R³)(R⁴))ₙ—, B is not unsubstituted phenyl or phenyl monosubstituted with methyl or phenyl trisubstituted with alkoxy.

2. A compound according to claim 1, wherein B is selected from the group consisting of phenyl; naphthyl; benzo[1,3]dioxol and phenyl substituted with from 1–3 substituents selected from the group consisting of halogen, hydroxy, lower-alkyl, lower-alkoxy, trifluoromethyl, cyano, di-lower-alkyl-amino, N-oxides of di-lower-alkyl-amino, phenyloxy, phenyl and methylsulphanyl.

3. A compound according to claim 2, wherein R¹ is chlorine, R² is hydrogen, p is 1 or 2, A is —CH₂C(CH₃)₂— and B is a benzene ring which is mono-, di- or tri-substituted.

4. A compound according to claim 3, selected from the group consisting of
N₁-(7-Chloro-quinolin-4-yl)-N₂-(3-chloro-benzyl)-2-methyl-propane-1,2-diamine,
N₁-(7-chloro-quinolin-4-yl)-N₂-(2-hydroxy-3-methoxy-benzyl)-2-methyl-propane-1,2-diamine,
N₁-(7-chloro-quinolin-4-yl)-N₂-(2-hydroxy-5-methoxy-benzyl)-2-methyl-propane-1,2-diamine,
N₁-(7-chloro-quinolin-4-yl)-N₂-(4-hydroxy-3-methoxy-benzyl)-2-methyl-propane-1,2-diamine,
N₁-(7-chloro-quinolin-4-yl)-N₂ (benzyl)-2-methyl-propane-1,2-diamine.

5. A compound according to claim 2, wherein R¹ is chlorine, R² is hydrogen, p is 1, A is cyclohexane-1,2-diyl or cyclohexane-1,4-diyl and B is a benzene ring which is unsubstituted or mono- or di-substituted.

6. A compound according to claim 5, selected from the group consisting of
(1S,2S)-N₁-(7-Chloro-quinolin-4-yl)-N₂-(benzyl)-cyclohexane-1,2-diamine,
(1S,2S)-N₁-(7-chloro-quinolin-4-yl)-N₂-(4-chloro-benzyl)-cyclohexane-1,2-diamine,
(1S,2S)-N₁-(7-chloro-quinolin-4-yl)-N₂-(4-dimethylamino-benzyl)-cyclo-hexane-1,2-diamine,
cis-N₁-(7-chloro-quinolin-4-yl)-N₄-(4-dimethylamino-benzyl)-cyclohexane-1,4-diamine,
cis-N₁-(7-chloro-quinolin-4-yl)-N₄-(benzyl)-cyclohexane-1,4-diamine,
cis-N₁-(7-chloro-quinolin-4-yl)-N₄-(3-chloro-benzyl)-cyclohexane-1,4-diamine,
cis-N₁-(7-chloro-quinolin-4-yl)-N₄-(2-hydroxy-4-methoxy-benzyl)-cyclohexane-1,4-diamine,
cis-N₁-(7-chloro-quinolin-4-yl)-N₄-(3,5-dimethoxy-benzyl)-cyclohexane-1,4-diamine,
cis-N₁-(7-chloro-quinolin-4-yl)-N₄-(4-methylsulphanyl-benzyl)-cyclohexane-1,4-diamine,
cis-N₁-(7-chloro-quinolin-4-yl)-N₄-(4-diethylamino-benzyl)-cyclohexane-1,4-diamine,
cis-N₁-(7-chloro-quinolin-4-yl)-N₄-(biphenyl-4-ylmethyl)-cyclohexane-1,4-diamine,
trans-N₁-(7-chloro-guinolin-4-yl)-N₄-[2-(3,5-dimethoxy-phenyl)-ethyl]-cyclohexane-1,4-diamine.
cis-N₁-(7-chloro-quinolin-4-yl)-N₄-(4-methoxy-benzyl)-cyclohexane-1,4-diamine,
trans-N₁-(7-chloro-guinolin-4-yl)-N₄-(4-dimethylamino-benzyl)-cyclohexane-1,4-diamine and trans-N₁-(7-chloro-guinolin-4-yl)-N₄-(2,6-difluoro-benzyl)-cyclohexane-1,4-diamine.

7. A pharmaceutical composition comprising a compound of the formula

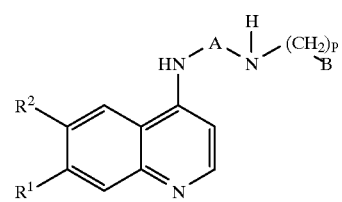

wherein
R¹ is halogen or trifluoromethyl;
R² is selected from the group consisting of hydrogen, halogen and trifluoromethyl;
A is

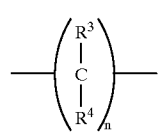

or $(C_5-C_6)$-cycloalkylene
n is 1–4;
R³ and R⁴ are each independently hydrogen or methyl;
p is 1–3;

B is aryl selected from phenyl, phenyl mono-, di-, or tri-substituted by substituent from the group consisting of halogen, hydroxy, lower alkyl, lower alkoxy, trifluoromethyl, cyano, di-lower alkylamino or their N-oxides, phenyloxy, phenyl, and methylsuphanyl, naphthyl, benzo[1,3]dioxol, or monocyclic aromatic heterocycle with 1 or 2 heteroatoms selected from N and O;

as well as pharmaceutically acceptable salts of basic compounds of formula I, wherein when A is —(C(R³)(R⁴))$_n$—, B is not unsubstituted phenyl or phenyl monosubstituted with methyl or phenyl trisubstituted with alkoxy, and a pharmaceutically inert carrier.

8. A pharmaceutical composition according to claim 7, wherein B is selected from the group consisting of phenyl; naphthyl; benzo[1,3]dioxol and phenyl substituted with from 1–3 substituents selected from the group consisting of halogen, hydroxy, lower-alkyl, lower-alkoxy, trifluoromethyl, cyano, di-lower-alkyl-amino, N-oxides of di-lower-alkyl-amino, phenyloxy, phenyl and methylsulphanyl.

9. A pharmaceutical composition according to claim 8, further comprising pharmaceutically inert, inorganic or organic carriers, preservatives, solubilizers, stabilizers, wetting agents, emulsifiers, sweeteners, colorants, flavorants, antioxidants and coating agents.

10. A method of the prevention or treatment of malaria wherein the malaria pathogens are either chloroquine-sensitive or chloroquine-resistant, comprising administering to a patient in case of such treatment an effective amount of a compound of the formula

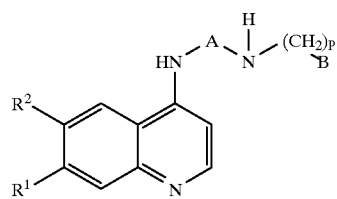

I wherein

R¹ is halogen or trifluoromethyl;

R² is selected from the group consisting of hydrogen, halogen and trifluoromethyl;

A is

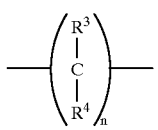

or (C₅–C₆)-cycloalkylene n is 1–4;

R³ and R⁴ are each independently hydrogen or methyl;

p is 1–3;

B is aryl selected from phenyl, phenyl mono-, di-, or tri-substituted by substituent from the group consisting of halogen, hydroxy, lower alkyl, lower alkoxy, trifluoromethyl, cyano, di-lower alkylamino or their N-oxides, phenyloxy, phenyl, and methylsuphanyl, naphthyl, benzo[1,3]dioxol, or monocyclic aromatic heterocycle with 1 or 2 heteroatoms selected from N and O;

as well as pharmaceutically acceptable salts of basic compounds of formula I, wherein when A is —(C(R³)(R⁴))$_n$—, B is not unsubstituted phenyl or phenyl monosubstituted with methyl or phenyl trisubstituted with alkoxy, and a pharmaceutically inert carrier.

11. The method of claim 10, wherein B is selected from the group consisting of phenyl; naphthyl; benzo[1,3]dioxol and phenyl substituted with from 1–3 substituents selected from the group consisting of halogen, hydroxy, lower-alkyl, lower-alkoxy, trifluoromethyl, cyano, di-lower-alkyl-amino, N-oxides of di-lower-alkyl-amino, phenyloxy, phenyl and methylsulphanyl.

12. The method of claim 11, wherein the effective amount is from about 10 mg to about 2.5g per day.

13. The compound of claim 1, wherein R¹ is chlorine, R² is hydrogen, p is 1, A is —CH₂C (CH₃)₂—.

14. The compound of claim 1, wherein R¹ is chlorine, R² is hydrogen, p is 2, A is cyclohexane-1,4-diyl and B is a disubstituted benzene ring.

15. The compound of claim 14, trans-N₁-(7-chloro-quinolin-4-yl)-N₄-(2-(3,5-dimethoxy-phenyl)-ethyl)-cyclohexane-1,4-diamine.

* * * * *

UNITED STATES PATENT AND TRADEMARK OFFICE
CERTIFICATE OF CORRECTION

PATENT NO. : 5,948,791
DATED : September 7, 1999
INVENTOR(S) : Hofheinz, et al.

It is certified that error appears in the above-identified patent and that said Letters Patent is hereby corrected as shown below:

IN THE CLAIMS:

Column 44, line 29: please insert the following omitted chemical formula:
--- $N_1$-(7-chloro-quinolin-4-yl)-$N_2$-(benzyl)-2-methyl-propane-1,2-diamine, --- ;

Column 44, line 30: "guinolin" should read --- quinolin --- ;

Column 44, line 31: "diamine." should read --- diamine, --- ;

Column 44, line 33: "diamine." should read --- diamine, --- ;

Column 44, line 34: "guinolin" should read --- quinolin --- ;

Column 44, line 36: "guinolin" should read --- quinolin --- .

Claim 10, Column 45, line 27: "the prevention or" should be omitted.

Signed and Sealed this

Thirteenth Day of February, 2001

Attest:

NICHOLAS P. GODICI

Attesting Officer
Acting Director of the United States Patent and Trademark Office